United States Patent
Svendsen et al.

(10) Patent No.: US 8,455,235 B2
(45) Date of Patent: Jun. 4, 2013

(54) PROTEASE VARIANTS FOR PHARMACEUTICAL USE

(75) Inventors: Allan Svendsen, Hoersholm (DK); Lars Beier, Lyngby (DK); Signe Eskildsen Larsen, Lyngby (DK); Thomas Lenhard, Lyngby (DK); Tanja Maria Rosenkilde Kjaer, Holte (DK); Peter Colin Gregory, Hannover (DE)

(73) Assignees: Novozymes A/S, Bagsvaerd (DK); Solvay Pharmaceuticals, GmbH, Hannover (DE)

( * ) Notice: Subject to any disclaimer, the term of this patent is extended or adjusted under 35 U.S.C. 154(b) by 181 days.

(21) Appl. No.: 12/745,652

(22) PCT Filed: Dec. 2, 2008

(86) PCT No.: PCT/EP2008/066646
§ 371 (c)(1),
(2), (4) Date: Aug. 3, 2010

(87) PCT Pub. No.: WO2009/071550
PCT Pub. Date: Jun. 11, 2009

(65) Prior Publication Data
US 2010/0322915 A1 Dec. 23, 2010

Related U.S. Application Data

(60) Provisional application No. 60/992,196, filed on Dec. 4, 2007.

(30) Foreign Application Priority Data

Dec. 4, 2007 (EP) .................................... 07122243

(51) Int. Cl.
*C12N 9/52* (2006.01)
*A61K 38/48* (2006.01)
*A23K 1/165* (2006.01)

(52) U.S. Cl.
USPC ......... 435/220; 435/198; 435/210; 424/94.64

(58) Field of Classification Search
None
See application file for complete search history.

(56) References Cited

U.S. PATENT DOCUMENTS

| | | | |
|---|---|---|---|
| 5,614,189 A | 3/1997 | Huge-Jensen | |
| 5,614,224 A | 3/1997 | Womack | |
| 6,051,220 A | 4/2000 | Scharpe | |
| 6,440,413 B1 | 8/2002 | Hooreman | |
| 2002/0061302 A1 | 5/2002 | Sander-Struckmeier et al. | |
| 2004/0057944 A1 | 3/2004 | Galle et al. | |
| 2008/0063774 A1* | 3/2008 | Aehle et al. ................... | 426/531 |

FOREIGN PATENT DOCUMENTS

| | | |
|---|---|---|
| JP | 2003-284571 A | 10/2003 |
| WO | WO 88/03947 | 6/1988 |
| WO | 97/00614 A1 | 1/1997 |
| WO | WO 97/37681 A1 | 10/1997 |
| WO | WO 00/54799 A2 | 9/2000 |
| WO | WO 01/58276 | 8/2001 |
| WO | WO 02/060474 A2 | 8/2002 |
| WO | WO 03/106667 A2 | 12/2003 |
| WO | WO 2004/111219 | 12/2004 |
| WO | WO 2004/111220 | 12/2004 |
| WO | WO 2004/111221 | 12/2004 |
| WO | WO 2004/111222 | 12/2004 |
| WO | WO 2004/111223 | 12/2004 |
| WO | WO 2005/035747 | 4/2005 |
| WO | WO 2005/115445 | 12/2005 |
| WO | WO 2005/123911 | 12/2005 |
| WO | WO 2006/136159 | 12/2006 |
| WO | WO 2006/136161 | 12/2006 |

OTHER PUBLICATIONS

Search Report issued in corresponding international application No. PCT/EP2008/066646 dated Feb. 26, 2009.
Amano Enzyme Inc, Digestive Enzyme Prozyme, Amano Products-05—, p. PZ1-PZ-7, Japan, 2000.
COBALT Alignment Tool (2011).
Lebenthal et al., Pancreas, vol. 9, No. 1, pp. 1-12 (1994).
Register of RU Medicaments, Encyclopedia of Medicaments, 10th Ed, Sr. Ed Vyshkovsky,Moscow, p. 637 (RLS-2003).

* cited by examiner

*Primary Examiner* — Manjunath Rao
*Assistant Examiner* — William W Moore
(74) *Attorney, Agent, or Firm* — Elias Lambiris

(57) ABSTRACT

The invention relates to novel variants of a protease derived from *Nocardiopsis* sp. (SEQ ID NO: 1) and closely related proteases, as well as their pharmaceutical use. The variants show improved performance in the treatment of pancreatic exocrine insufficiency (PEI). The variants may be combined with a lipase and/or an amylase. Other examples of medical indications are: Treatment of digestive disorders, pancreatitis, cystic fibrosis, diabetes type I, and/or diabetes type II.

17 Claims, No Drawings

SEQUENCE LISTING

<160> NUMBER OF SEQ ID NOS: 11

<210> SEQ ID NO 1
<211> LENGTH: 188
<212> TYPE: PRT
<213> ORGANISM: Nocardiopsis sp.
<220> FEATURE:
<221> NAME/KEY: mat_peptide
<222> LOCATION: (1)..(188)

<400> SEQUENCE: 1

```
Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185
```

<210> SEQ ID NO 2
<211> LENGTH: 274
<212> TYPE: PRT
<213> ORGANISM: Artificial Sequence
<220> FEATURE:
<223> OTHER INFORMATION: Variant (T231R+N233R) of Humicola lanuginosa lipase
<220> FEATURE:
<221> NAME/KEY: PROPEP

```
<222> LOCATION: (1)..(5)
<220> FEATURE:
<221> NAME/KEY: mat_peptide
<222> LOCATION: (6)..(274)

<400> SEQUENCE: 2

Ser Pro Ile Arg Arg Glu Val Ser Gln Asp Leu Phe Asn Gln Phe Asn
 -5              -1   1               5                      10

Leu Phe Ala Gln Tyr Ser Ala Ala Tyr Cys Gly Lys Asn Asn Asp
             15              20              25

Ala Pro Ala Gly Thr Asn Ile Thr Cys Thr Gly Asn Ala Cys Pro Glu
             30              35              40

Val Glu Lys Ala Asp Ala Thr Phe Leu Tyr Ser Phe Glu Asp Ser Gly
 45              50              55

Val Gly Asp Val Thr Gly Phe Leu Ala Leu Asp Asn Thr Asn Lys Leu
 60              65              70                      75

Ile Val Leu Ser Phe Arg Gly Ser Arg Ser Ile Glu Asn Trp Ile Gly
             80              85                      90

Asn Leu Asn Phe Asp Leu Lys Glu Ile Asn Asp Ile Cys Ser Gly Cys
             95              100             105

Arg Gly His Asp Gly Phe Thr Ser Ser Trp Arg Ser Val Ala Asp Thr
             110             115             120

Leu Arg Gln Lys Val Glu Asp Ala Val Arg Glu His Pro Asp Tyr Arg
 125             130             135

Val Val Phe Thr Gly His Ser Leu Gly Gly Ala Leu Ala Thr Val Ala
 140             145             150             155

Gly Ala Asp Leu Arg Gly Asn Gly Tyr Asp Ile Asp Val Phe Ser Tyr
             160             165             170

Gly Ala Pro Arg Val Gly Asn Arg Ala Phe Ala Glu Phe Leu Thr Val
             175             180             185

Gln Thr Gly Gly Thr Leu Tyr Arg Ile Thr His Thr Asn Asp Ile Val
             190             195             200

Pro Arg Leu Pro Pro Arg Glu Phe Gly Tyr Ser His Ser Ser Pro Glu
 205             210             215

Tyr Trp Ile Lys Ser Gly Thr Leu Val Pro Val Arg Arg Arg Asp Ile
 220             225             230             235

Val Lys Ile Glu Gly Ile Asp Ala Thr Gly Gly Asn Asn Gln Pro Asn
             240             245             250

Ile Pro Asp Ile Pro Ala His Leu Trp Tyr Phe Gly Leu Ile Gly Thr
             255             260             265

Cys Leu

<210> SEQ ID NO 3
<211> LENGTH: 481
<212> TYPE: PRT
<213> ORGANISM: Artificial Sequence
<220> FEATURE:
<223> OTHER INFORMATION: Variant of Bacillus licheniformis amylase
<220> FEATURE:
<221> NAME/KEY: mat_peptide
<222> LOCATION: (1)..(481)

<400> SEQUENCE: 3

Val Asn Gly Thr Leu Met Gln Tyr Phe Glu Trp Tyr Thr Pro Asn Asp
 1               5                  10                   15

Gly Gln His Trp Lys Arg Leu Gln Asn Asp Ala Glu His Leu Ser Asp
             20              25              30

Ile Gly Ile Thr Ala Val Trp Ile Pro Pro Ala Tyr Lys Gly Thr Ser
```

```
                35                    40                   45
Gln Ala Asp Val Gly Tyr Gly Ala Tyr Asp Leu Tyr Asp Leu Gly Glu
         50                    55                   60
Phe His Gln Lys Gly Thr Val Arg Thr Lys Tyr Gly Thr Lys Gly Glu
65                    70                   75                   80
Leu Gln Ser Ala Ile Lys Ser Leu His Ser Arg Asp Ile Asn Val Tyr
                 85                   90                   95
Gly Asp Val Val Ile Asn His Lys Gly Gly Ala Asp Ala Thr Glu Asp
                100                  105                  110
Val Thr Ala Val Glu Val Asp Pro Ala Asp Arg Asn Arg Val Ile Ser
            115                  120                  125
Gly Glu His Leu Ile Lys Ala Trp Thr His Phe His Phe Pro Gly Arg
        130                  135                  140
Gly Ser Thr Tyr Ser Asp Phe Lys Trp Tyr Trp Tyr His Phe Asp Gly
145                  150                  155                  160
Thr Asp Trp Asp Glu Ser Arg Lys Leu Asn Arg Ile Tyr Lys Phe Gln
                165                  170                  175
Gly Lys Thr Trp Asp Trp Glu Val Ser Asn Glu Phe Gly Asn Tyr Asp
            180                  185                  190
Tyr Leu Met Tyr Ala Asp Ile Asp Tyr Asp His Pro Asp Val Val Ala
        195                  200                  205
Glu Ile Lys Arg Trp Gly Thr Trp Tyr Ala Asn Glu Leu Gln Leu Asp
        210                  215                  220
Gly Phe Arg Leu Asp Ala Val Lys His Ile Lys Phe Ser Phe Leu Arg
225                  230                  235                  240
Asp Trp Val Asn His Val Arg Glu Lys Thr Gly Lys Glu Met Phe Thr
                245                  250                  255
Val Ala Glu Tyr Trp Ser Asn Asp Leu Gly Ala Leu Glu Asn Tyr Leu
            260                  265                  270
Asn Lys Thr Asn Phe Asn His Ser Val Phe Asp Val Pro Leu His Tyr
        275                  280                  285
Gln Phe His Ala Ala Ser Thr Gln Gly Gly Gly Tyr Asp Met Arg Lys
        290                  295                  300
Leu Leu Asn Gly Thr Val Val Ser Lys His Pro Leu Lys Ser Val Thr
305                  310                  315                  320
Phe Val Asp Asn His Asp Thr Gln Pro Gly Gln Ser Leu Glu Ser Thr
                325                  330                  335
Val Gln Thr Trp Phe Lys Pro Leu Ala Tyr Ala Phe Ile Leu Thr Arg
            340                  345                  350
Glu Ser Gly Tyr Pro Gln Val Phe Tyr Gly Asp Met Tyr Gly Thr Lys
        355                  360                  365
Gly Asp Ser Gln Arg Glu Ile Pro Ala Leu Lys His Lys Ile Glu Pro
        370                  375                  380
Ile Leu Lys Ala Arg Lys Gln Tyr Ala Tyr Gly Ala Gln His Asp Tyr
385                  390                  395                  400
Phe Asp His His Asp Ile Val Gly Trp Thr Arg Glu Gly Asp Ser Ser
                405                  410                  415
Val Ala Asn Ser Gly Leu Ala Ala Leu Ile Thr Asp Gly Pro Gly Gly
            420                  425                  430
Ala Lys Arg Met Tyr Val Gly Arg Gln Asn Ala Gly Glu Thr Trp His
        435                  440                  445
Asp Ile Thr Gly Asn Arg Ser Glu Pro Val Val Ile Asn Ser Glu Gly
450                  455                  460
```

```
Trp Gly Glu Phe His Val Asn Gly Gly Ser Val Ser Ile Tyr Val Gln
465                 470                 475                 480

Arg

<210> SEQ ID NO 4
<211> LENGTH: 483
<212> TYPE: PRT
<213> ORGANISM: Artificial Sequence
<220> FEATURE:
<223> OTHER INFORMATION: Variant of Bacillus sp. amylase
<220> FEATURE:
<221> NAME/KEY: mat_peptide
<222> LOCATION: (1)..(483)

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Phe Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Val Gln Lys His Pro
305                 310                 315                 320

Met His Ala Val Thr Phe Val Asp Asn His Asp Ser Gln Pro Glu Glu
                325                 330                 335
```

```
Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
            405                 410                 415

Thr Ala His Pro Asn Ser Gly Leu Ala Thr Ile Met Ser Asp Gly Ala
        420                 425                 430

Gly Gly Asn Lys Trp Met Phe Val Gly Arg Asn Lys Ala Gly Gln Val
    435                 440                 445

Trp Thr Asp Ile Thr Gly Asn Lys Ala Gly Thr Val Thr Ile Asn Ala
450                 455                 460

Asp Gly Trp Gly Asn Phe Ser Val Asn Gly Gly Ser Val Ser Ile Trp
465                 470                 475                 480

Val Asn Lys

<210> SEQ ID NO 5
<211> LENGTH: 513
<212> TYPE: PRT
<213> ORGANISM: Artificial Sequence
<220> FEATURE:
<223> OTHER INFORMATION: Variant of Bacillus stearothermophilus amylase
<220> FEATURE:
<221> NAME/KEY: mat_peptide
<222> LOCATION: (1)..(486)

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
            180                 185                 190

Asn Tyr Asp Tyr Leu Met Tyr Ala Asp Leu Asp Met Asp His Pro Glu
```

```
            195                 200                 205
Val Val Thr Glu Leu Lys Asn Trp Gly Lys Trp Tyr Val Asn Thr Thr
210                 215                 220
Asn Ile Asp Gly Phe Arg Leu Asp Ala Val Lys His Ile Lys Phe Ser
225                 230                 235                 240
Phe Phe Pro Asp Trp Leu Ser Tyr Val Arg Ser Gln Thr Gly Lys Pro
                245                 250                 255
Leu Phe Thr Val Gly Glu Tyr Trp Ser Tyr Asp Ile Asn Lys Leu His
                260                 265                 270
Asn Tyr Ile Thr Lys Thr Asp Gly Thr Met Ser Leu Phe Asp Ala Pro
                275                 280                 285
Leu His Asn Lys Phe Tyr Thr Ala Ser Lys Ser Gly Gly Ala Phe Asp
290                 295                 300
Met Arg Thr Leu Met Thr Asn Thr Leu Met Lys Asp Gln Pro Thr Leu
305                 310                 315                 320
Ala Val Thr Phe Val Asp Asn His Asp Thr Glu Pro Gly Gln Ala Leu
                325                 330                 335
Gln Ser Trp Val Asp Pro Trp Phe Lys Pro Leu Ala Tyr Ala Phe Ile
                340                 345                 350
Leu Thr Arg Gln Glu Gly Tyr Pro Cys Val Phe Tyr Gly Asp Tyr Tyr
            355                 360                 365
Gly Ile Pro Gln Tyr Asn Ile Pro Ser Leu Lys Ser Lys Ile Asp Pro
370                 375                 380
Leu Leu Ile Ala Arg Arg Asp Tyr Ala Tyr Gly Thr Gln His Asp Tyr
385                 390                 395                 400
Leu Asp His Ser Asp Ile Ile Gly Trp Thr Arg Glu Gly Gly Thr Glu
                405                 410                 415
Lys Pro Gly Ser Gly Leu Ala Ala Leu Ile Thr Asp Gly Pro Gly Gly
                420                 425                 430
Ser Lys Trp Met Tyr Val Gly Lys Gln His Ala Gly Lys Val Phe Tyr
            435                 440                 445
Asp Leu Thr Gly Asn Arg Ser Asp Thr Val Thr Ile Asn Ser Asp Gly
450                 455                 460
Trp Gly Glu Phe Lys Val Asn Gly Gly Ser Val Ser Val Trp Val Pro
465                 470                 475                 480
Arg Lys Thr Thr Val Ser Thr Ile Ala Arg Pro Ile Thr Thr Arg Pro
                485                 490                 495
Trp Thr Gly Glu Phe Val Arg Trp Thr Glu Pro Arg Leu Val Ala Trp
                500                 505                 510
Pro

<210> SEQ ID NO 6
<211> LENGTH: 188
<212> TYPE: PRT
<213> ORGANISM: Artificial Sequence
<220> FEATURE:
<223> OTHER INFORMATION: Variant E125D of Nocardiopsis sp. protease
<220> FEATURE:
<221> NAME/KEY: mat_peptide
<222> LOCATION: (1)..(188)

<400> SEQUENCE: 6

Ala Asp Ile Ile Gly Gly Leu Ala Tyr Thr Met Gly Gly Arg Cys Ser
1               5                   10                  15
Val Gly Phe Ala Ala Thr Asn Ala Ala Gly Gln Pro Gly Phe Val Thr
                20                  25                  30
```

```
Ala Gly His Cys Gly Arg Val Gly Thr Gln Val Thr Ile Gly Asn Gly
            35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Gly Trp His Cys Gly
                    100                 105                 110

Thr Ile Gln Ala Arg Gly Gln Ser Val Ser Tyr Pro Asp Gly Thr Val
            115                 120                 125

Thr Asn Met Thr Arg Thr Thr Val Cys Ala Glu Pro Gly Asp Ser Gly
130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                    165                 170                 175

Pro Met Val Asn Ser Trp Gly Val Arg Leu Arg Thr
            180                 185

<210> SEQ ID NO 7
<211> LENGTH: 188
<212> TYPE: PRT
<213> ORGANISM: Artificial Sequence
<220> FEATURE:
<223> OTHER INFORMATION: Variant R38T of Nocardiopsis sp. protease
<220> FEATURE:
<221> NAME/KEY: mat_peptide
<222> LOCATION: (1)..(188)

<400> SEQUENCE: 7

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
                20                  25                  30

Ala Gly His Cys Gly Thr Val Gly Thr Gln Val Thr Ile Gly Asn Gly
            35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Gly Trp His Cys Gly
                    100                 105                 110

Thr Ile Gln Ala Arg Gly Gln Ser Val Ser Tyr Pro Glu Gly Thr Val
            115                 120                 125

Thr Asn Met Thr Arg Thr Thr Val Cys Ala Glu Pro Gly Asp Ser Gly
130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                    165                 170                 175

Pro Met Val Asn Ser Trp Gly Val Arg Leu Arg Thr
            180                 185
```

```
<210> SEQ ID NO 8
<211> LENGTH: 188
<212> TYPE: PRT
<213> ORGANISM: Artificial Sequence
<220> FEATURE:
<223> OTHER INFORMATION: Variant (T44K+S99P) of Nocardiopsis sp.
      protease
<220> FEATURE:
<221> NAME/KEY: mat_peptide
<222> LOCATION: (1)..(188)

<400> SEQUENCE: 8

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Lys Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Pro Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 9
<211> LENGTH: 188
<212> TYPE: PRT
<213> ORGANISM: Artificial Sequence
<220> FEATURE:
<223> OTHER INFORMATION: Variant S69T of Nocardiopsis sp. protease
<220> FEATURE:
<221> NAME/KEY: mat_peptide
<222> LOCATION: (1)..(188)

<400> SEQUENCE: 9

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Thr Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95
```

```
Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Thr Thr Phe Tyr Gln Glu Val Thr
                165                 170                 175

Pro Met Val Asn Ser Trp Gly Val Arg Leu Arg Thr
            180                 185

<210> SEQ ID NO 10
<211> LENGTH: 188
<212> TYPE: PRT
<213> ORGANISM: Artificial Sequence
<220> FEATURE:
<223> OTHER INFORMATION: Variant R165S of Nocardiopsis sp. protease
<220> FEATURE:
<221> NAME/KEY: mat_peptide
<222> LOCATION: (1)..(188)

<400> SEQUENCE: 10

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Ser Thr Gly Thr Thr Phe Tyr Gln Glu Val Thr
                165                 170                 175

Pro Met Val Asn Ser Trp Gly Val Arg Leu Arg Thr
            180                 185

<210> SEQ ID NO 11
<211> LENGTH: 188
<212> TYPE: PRT
<213> ORGANISM: Artificial Sequence
<220> FEATURE:
<223> OTHER INFORMATION: Variant (S69T+E125D) of Nocardiopsis sp.
      protease
<220> FEATURE:
<221> NAME/KEY: mat_peptide
<222> LOCATION: (1)..(188)

<400> SEQUENCE: 11
```

-continued

```
Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
                20                  25                  30

Ala Gly His Cys Gly Arg Val Gly Thr Gln Val Thr Ile Gly Asn Gly
            35                  40                  45

Arg Gly Val Phe Glu Gln Ser Val Phe Pro Gly Asn Asp Ala Ala Phe
    50                  55                  60

Val Arg Gly Thr Thr Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
                100                 105                 110

Thr Ile Gln Ala Arg Gly Gln Ser Val Ser Tyr Pro Asp Gly Thr Val
            115                 120                 125

Thr Asn Met Thr Arg Thr Thr Val Cys Ala Glu Pro Gly Asp Ser Gly
        130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
                180                 185
```

PROTEASE VARIANTS FOR PHARMACEUTICAL USE

CROSS-REFERENCE TO RELATED APPLICATIONS

This application is a 35 U.S.C. 371 national application of PCT/EP2008/066646 filed Dec. 2, 2008, which claims priority to the benefit under 35 U.S.C. 119 of European application no. 07122243.4 filed Dec. 4, 2007 and U.S. provisional application no. 60/992,196 filed Dec. 4, 2007, the contents of which are fully incorporated herein by reference.

REFERENCE TO A SEQUENCE LISTING

This application contains a Sequence Listing in computer readable form. The computer readable form is incorporated herein by reference.

TECHNICAL FIELD

The present invention relates to a protease having at least 90% identity to amino acids 1-188 of SEQ ID NO: 1, and which, as compared to amino acids 1-188 of SEQ ID NO: 1, comprises at least one substitution selected from the following substitutions: A1T; I3V; G12; R14I; T22A; N23D; G34A; R38; T41A; T44K; N47; G48D; E53K; Q54L,D; T68A,R,S; S69T; L73P; V88A; S99P; P124L; E125; M131V; T151I; R165; and T166A. The protease of SEQ ID NO: 1 is a wild type protease from *Nocardiopsis* sp.

The invention also relates to the pharmaceutical use of these proteases, optionally in combination with a lipase and/or an amylase. Examples of medical indications are: Treatment of digestive disorders, pancreatic exocrine insufficiency (PEI), pancreatitis, cystic fibrosis, diabetes type I, and/or diabetes type II.

BACKGROUND ART

Several commercial medicaments in the form of pancreatic enzyme supplements are known for the treatment of pancreatic exocrine insufficiency. The active ingredients of these products are digestive enzymes, mainly amylase, lipase and protease, which are normally produced in the pancreas and excreted to the upper part of the small intestine (the duodenum). The enzymes used in such medicaments derive from bovine or swine pancreas.

WO 2005/115445 describes the use of the protease of SEQ ID NO: 1 and related proteases for pharmaceutical use, e.g. for the treatment of PEI.

WO 2006/136159 describes the use of the lipase of SEQ ID NO: 2 and related lipases for pharmaceutical use, e.g. for the treatment of PEI.

WO 2006/136161 describes the use of the amylases of SEQ ID NO: 3, 4, and 5 and related amylases for pharmaceutical use, e.g. for the treatment of PEI.

The protease derived from *Nocardiopsis* sp. (SEQ ID NO: 1), as well as its preparation and various industrial applications thereof are described in WO 88/03947 and WO 01/58276. Related proteases are described in WO 2004/111220, WO 2004/111222, WO 2004/111223, WO 2004/111221, WO 2005/035747, WO 2004/111219, WO 2005/123911, and JP 2003284571-A (GENESEQP:ADF43564).

The present invention provides novel proteases of an improved performance, e.g. of an improved apparent protein digestibility in vivo, an improved pH-ratio (pH5.6/pH8), and/or a reduced toxicity.

SUMMARY OF THE INVENTION

The present invention relates to a protease having at least 90% identity to amino acids 1-188 of SEQ ID NO: 1, and which, as compared to amino acids 1-188 of SEQ ID NO: 1, comprises at least one substitution selected from the following substitutions: A1T; I3V; G12; R14I; T22A; N23D; G34A; R38; T41A; T44K; N47; G48D; E53K; Q54L,D; T68A,R,S; S69T; L73P; V88A; S99P; P124L; E125; M131V; T151I; R165; and T166A.

The invention furthermore relates to such proteases for use as a medicament, optionally in combination with a lipase and/or an amylase.

Still further, the invention relates to the use of such proteases, optionally in combination with a lipase and/or an amylase, for the manufacture of a medicament for the treatment of digestive disorders, pancreatic exocrine insufficiency, pancreatitis, cystic fibrosis, diabetes type I, and/or diabetes type II.

The invention also relates to such proteases, optionally in combination with a lipase and/or an amylase, for use in the treatment of digestive disorders, pancreatic exocrine insufficiency, pancreatitis, cystic fibrosis, diabetes type I, and/or diabetes type II.

The invention furthermore relates to pharmaceutical compositions comprising such proteases, optionally in combination with a lipase and/or an amylase, together with at least one pharmaceutically acceptable auxiliary material.

Finally, the invention relates to methods for the treatment of digestive disorders, pancreatic exocrine insufficiency, pancreatitis, cystic fibrosis, diabetes type I, and/or diabetes type II, by administering a therapeutically effective amount of such proteases, optionally in combination with a lipase and/or an amylase.

DETAILED DESCRIPTION OF THE INVENTION

Enzymes

The term "protease" is defined herein as a polypeptide having protease activity. A protease is an enzyme that hydrolyses peptide bonds. It includes any enzyme belonging to the EC 3.4 enzyme group (including each of the thirteen subclasses thereof, these enzymes being in the following referred to as "belonging to the EC 3.4.-.- group"). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see, e.g., the World Wide Web at http://www.chem.qmul.ac.uk/iubmb/enzyme.

In particular embodiments, the proteases of the present invention are selected from the group consisting of proteases derived from strains of *Nocardiopsis*.

The relatedness between two amino acid sequences is described by the parameter "identity".

For purposes of the present invention, the two amino acid sequences are aligned using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1-188 of SEQ ID NO: 6) and a different amino acid sequence ("foreign sequence"; e.g. amino acids 1-188 of SEQ ID NO: 1) is calculated as the number of exact matches in this alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g. the length of SEQ ID NO: 6 is 188).

In the, purely hypothetical, alignment example below, the overlap is the amino acid sequence "HTWGER-NL" of Sequence 1; or the amino acid sequence "HGWGEDANL" of Sequence 2. In the example a gap is indicated by a "-".

Hypothetical alignment example:

```
Sequence 1:    ACMSHTWGER-NL
                   | ||| ||
Sequence 2:        HGWGEDANLAMNPS
```

Accordingly, the percentage of identity of Sequence 1 to Sequence 2 is 6/12=0.5, corresponding to 50%.

In a particular embodiment, the percentage of identity of an amino acid sequence of a polypeptide with, or to, e.g., amino acids 1-188 of SEQ ID NO: 1 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention such as amino acids 1-269 of SEQ ID NO: 2 is calculated in an analogous way.

In additional particular embodiments, the protease of the invention has a degree of identity to amino acids 1-188 of SEQ ID NO: 1 of at least 90%, at least 91%, or at least 92%; at least 93%, at least 94%, at least 95%, at least 96%, at least 97%, at least 98%, or at least 99%.

In the present invention, a specific numbering of amino acid residue positions is employed. The numbering system originates from the amino acid sequence of the protease disclosed in SEQ ID NO: 1, aligned using the Needle program with substitution matrix BLOSUM62, gap opening penalty 10, and gap extension penalty 0.5 (as described above) with the amino acid sequence of another protease.

For an amino acid substitution, as compared to SEQ ID NO: 1, the following nomenclature is used: Original amino acid (in SEQ ID NO: 1), position (in alignment), substituted amino acid (in the other protease). Accordingly, the substitution of glutamic acid (E) in SEQ ID NO: 1 with aspartic acid (D) in e.g. SEQ ID NO: 6 at position 125, by reference to SEQ ID NO: 1, is designated as "E125D". Multiple mutations are separated by addition marks ("+"), e.g., "T44K+S99P", representing mutations at positions 44 and 99 substituting threonine (T) with lysine (K), and serine (S) with proline (P), respectively (as e.g. in SEQ ID NO: 8). Furthermore expressions such as G12D,N,H mean that glycine (G) in position 12 is exchanged either by aspartic acid (D), asparagine (N), or histidine (H).

Substitution in position 12 in SEQ ID NO: 1 of glycine to any other amino acid is designated "G12".

Substitution in position 38 in SEQ ID NO: 1 of arginine to any other amino acid is designated "R38".

Substitution in position 47 in SEQ ID NO: 1 of asparagine to any other amino acid is designated "N47".

Substitution in position 125 in SEQ ID NO: 1 of glutamic acid to any other amino acid is designated "E125".

Substitution in position 165 in SEQ ID NO: 1 of arginine to any other amino acid is designated "R165".

In further particular embodiments, the protease of the invention is acid-stable, which means that the protease activity of the pure protease enzyme, in a dilution corresponding to $A_{280}=1.0$, and following incubation for 2 hours at 37° C. in the following buffer: 100 mM succinic acid, 100 mM HEPES, 100 mM CHES, 100 mM CABS, 1 mM $CaCl_2$, 150 mM KCl, 0.01% Triton® X-100, pH 3.5; is at least 40% (or at least 45, 50, 55, 60, 65, 70, 75, 80, 85, 90, 95, or at least 97%) of the reference activity, as measured using the assay described in Example 2C of WO 01/58276 (substrate: Suc-AAPF-pNA, pH 9.0, 25° C.). The term reference activity refers to the protease activity of the same protease, following incubation in pure form, in a dilution corresponding to $A_{280}=1.0$, for 2 hours at 5° C. in the following buffer: 100 mM succinic acid, 100 mM HEPES, 100 mM CHES, 100 mM CABS, 1 mM $CaCl_2$, 150 mM KCl, 0.01% Triton® X-100, pH 9.0, wherein the activity is determined as described above. The term $A_{280}=1.0$ means such concentration (dilution) of said pure protease which gives rise to an absorption of 1.0 at 280 nm in a 1 cm path length cuvette relative to a buffer blank. The term pure protease refers to a sample with a $A_{280}/A_{260}$ ratio above or equal to 1.70 (see Example 2E of WO 01/58276), and which by a scan of a Coomassie stained SDS-PAGE gel is measured to have at least 95% of its scan intensity in the band corresponding to said protease (see Example 2A of WO 01/58276).

Preferred Proteases of the Invention:

A protease having at least 90% identity to amino acids 1-188 of SEQ ID NO: 1, and which, as compared to amino acids 1-188 of SEQ ID NO: 1, comprises at least one substitution selected from the following substitutions: A1T; I3V; G12; R14I; T22A; N23D; G34A; R38; T41A; T44K; N47; G48D; E53K; Q54L,D; T68A,R,S; S69T; L73P; V88A; S99P; P124L; E125; M131V; T151I; R165; and T166A.

A protease having at least 90% identity to amino acids 1-188 of SEQ ID NO: 1, and which, as compared to amino acids 1-188 of SEQ ID NO: 1, comprises at least one substitution selected from the following substitutions: G12D,N,H; R38T; N47H,T,S; E125D and R165S,H,G,T.

A protease having at least 90% identity to amino acids 1-188 of SEQ ID NO: 1, and which, as compared to amino acids 1-188 of SEQ ID NO: 1, comprises at least one substitution: G12D,N,H; in particular G12D.

A protease having at least 90% identity to amino acids 1-188 of SEQ ID NO: 1, and which, as compared to amino acids 1-188 of SEQ ID NO: 1, comprises at least one substitution: N47H,T,S; in particular N47H.

A protease having at least 90% identity to amino acids 1-188 of SEQ ID NO: 1, and which, as compared to amino acids 1-188 of SEQ ID NO: 1, comprises at least one substitution: R165S,H,G,T; in particular N165H.

A protease having at least 90% identity to amino acids 1-188 of SEQ ID NO: 1, and which, as compared to amino acids 1-188 of SEQ ID NO: 1, comprises at least one substitution selected from the following substitutions or combinations of substitutions: G12D; and (N47H+G48D).

A protease having at least 90% identity to amino acids 1-188 of SEQ ID NO: 1, and which, as compared to amino acids 1-188 of SEQ ID NO: 1, comprises at least one substitution selected combinations of substitutions: (T41A+T68R+ V88A); (G12N+T22A+N23D+N47T+R165H); and (R14I+ R38T+T151I).

A protease having at least 90% identity to amino acids 1-188 of SEQ ID NO: 1, and which, as compared to amino acids 1-188 of SEQ ID NO: 1, comprises at least one substitution selected from the following substitutions or combinations of substitutions: R38T, (T44K+S99P), S69T, (S69T+E125D), E125D, and R165S.

A protease having at least 90% identity to amino acids 1-188 of SEQ ID NO: 1, and which, as compared to amino acids 1-188 of SEQ ID NO: 1, comprises at least one of the following substitutions or combinations of substitutions: R38T; T44K and S99P; S69T; S69T and E125D; E125D; and R165S.

A protease, which, as compared to amino acids 1-188 of SEQ ID NO: 1, comprises at least one of the following substitutions: A1T; I3V; G12; R14I; T22A; N23D; G34A; R38; T41A; T44K; N47; G48D; E53K; Q54L,D; T68A,R,S; S69T; L73P; V88A; S99P; P124L; E125; M131V; T151I; R165; and T166A; and which furthermore is selected from the group consisting of:
(a) a protease comprising, preferably having, an amino acid sequence having at least 90% identity to amino acids 1-188 of SEQ ID NO: 1;
(b) a protease encoded by a polynucleotide that hybridizes under very low (preferably low, medium, medium-high, high, or most preferably very high) stringency conditions with (i) the coding sequence of SEQ ID NO: 1 (nucleotides 900-1463 of SEQ ID NO: 1 of WO 2005/035747, hereby incorporated by reference), or (ii) a full-length complementary strand of (i); and
(c) a variant comprising in addition a substitution, deletion, and/or insertion of one or more (e.g., several) amino acids of the mature polypeptide of SEQ ID NO: 1, preferably of a conservative nature.

Very low to very high stringency conditions are defined as prehybridization and hybridization at 42° C. in 5×SSPE, 0.3% SDS, 200 microg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

Amino acid changes of a conservative nature do not significantly affect the folding and/or activity of the protein, and include small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

The total number of alterations in the variant preferably is eighteen, seventeen, or sixteen. More preferably the total number of alterations is fifteen, even more preferably fourteen, even more preferably thirteen, even more preferably twelve, even more preferably eleven, even more preferably ten, even more preferably nine, even more preferably eight, even more preferably seven, even more preferably six, even more preferably five, even more preferably four, even more preferably three, even more preferably two, and most preferably one amino acid.

A variant produced by shuffling one or more polynucleotides encoding one or more homologous parent proteases, wherein the variant comprises an alteration at one or more positions corresponding to one or more positions in a parent protease selected from the group consisting of: Position 38, 44, 69, 99, 125, and 165, wherein the alteration(s) independently corresponds to a substitution of the amino acid which occupies the position, and wherein the variant has protease activity.

The term "parent" protease means a protease to which modifications, e.g., substitution(s), insertion(s), deletion(s), and/or truncation(s), are made to produce the enzyme variants of the invention. This term also refers to the polypeptide with which a variant is compared and aligned. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. A parent may also be an allelic variant which is a polypeptide encoded by any of two or more alternative forms of a gene occupying the same chromosomal locus.

The term "shuffling" means recombination of nucleotide sequence(s) between two or more homologous nucleotide sequences resulting in recombined nucleotide sequences (i.e., nucleotide sequences having been subjected to a shuffling cycle) having a number of nucleotides exchanged, in comparison to the starting nucleotide sequences.

The proteases and protease variants according to each of the above examples and additional examples are preferably used in the combinations, uses, compositions and methods of the invention as set out herein and in the claims.

Protein Digestibility In Vivo, pH-Ratio (pH5.6/pH8), and/or a Reduced Toxicity.

The proteases and protease variants of the invention exhibit an improved performance, e.g. an improved apparent protein digestibility in vivo, an improved/altered pH-ratio (pH5.6/pH8), and/or a reduced toxicity.

The apparent protein digestibility in vivo may be determined in female Göttingen minipigs (Ellegaard) with induced PEI. The pigs are fed two meals per day containing 21.3% protein, 51.9% starch, 2.6% fat, preferably composed as described in Example 4. The pigs are allowed free access to water and preferably housed in cages on a 12:12 h light-dark cycle. The pigs are first fed a single 250 g test meal mixed with 1 liter of water, 0.625 g $Cr_2O_3$ (marker) into which differing amounts of reference protease of SEQ ID NO: 1 (0 mg, 20 mg, 50 mg and 120 mg enzyme protein/meal) are mixed immediately before feeding. For the trial the protease of the invention is dosed 20 mg, 50 mg and 120 mg/meal. Ileal chyme is collected on ice for a total of 8 h after first appearance of the meal marker in the ileum (green chyme) and stored at −20° C. before analysis. At least one day washout is allowed between separate determinations. The frozen ileal chyme samples are freeze-dried, milled and analysed for dry matter (DM) and crude protein. DM is estimated by weight after freeze-drying followed by 8 h incubation at 103° C. Crude protein is calculated as nitrogen (N) multiplied by a factor 6.25. The nitrogen content is determined by combustion, preferably with the Dumas combustion method, more preferably using a "Vario MAX CNS" Elemental Analyzer. $Cr_2O_3$ is oxidized to chromate and chromium content calculated via extinction at 365 nm. The apparent pre-caecal protein digestibility is calculated according to the formula shown in Example 4, in which $Cr_2O_3$ and protein are expressed as g/100 g dry matter.

For the proteases of the invention, the digestibility (such as the apparent pre-caecal protein digestibility) is preferably improved as compared to the digestibility of the reference protease in at least one of the dosages 20, 50 and 120 mg enzyme protein/meal. The improvement is preferably at least 1%, at least 2%, at least 3%, at least 4%, at least 5%, at least 6%, at least 7%, at least 8%, at least 9%, or at least 10%. More preferably, the improvement is at least 11%, at least 12%, at least 13%, at least 14%, at least 15%, at least 16%, at least 17%, at least 18%, at least 19%, or at least 20%. Even more preferably, the improvement is at least 21%, at least 22%, at least 23%, at least 24%, at least 25%, or at least 26%.

Furthermore, the amount (mg) of protease required to achieve 50% and 60% protein digestibility (% CNA), respectively, may be extrapolated from the individual regression curves (apparent pre-caecal protein digestibility versus enzyme dosage). Improvement factors 50 and 60 (IF50 and IF60) are calculated by dividing the amount (mg) of reference protease required to achieve 50% and 60% protein digestibility (% CNA), by the amount (mg) of variant protease required to achieve 50% and 60% protein digestibility (% CNA), respectively. Thus, for the reference protease IF50 and IF60 are both 1.00.

For the proteases of the invention, the IF50 and/or IF60 values is/are preferably at least 1.05, at least 1.10, at least 1.15, at least 1.20, at least 1.25, at least 1.30, at least 1.35, at least 1.40, at least 1.45, or at least 1.50.

For more details, see Example 4.

The pH-ratio is determined with casein as a substrate, more in particular with a casein derivative labelled with a suitable red-fluorescent dye, which is preferably pH-insensitive (e.g. in the area of pH 5.6-8.0). The increase in fluorescence is proportional to the protease activity. A preferred pH 8.0 assay buffer is 100 mM Tris/base, and a preferred pH 5.6 assay buffer can be prepared by mixing 25 ml 0.2 M succinic acid with 37.5 ml 0.2 M NaOH. Incubation takes place for a suitable time period (e.g. 60 minutes), at a suitable temperature (e.g. room temperature, e.g. 22° C.). A preferred fluorescent dye is BODIPY TR-X in which case the resulting fluorescent peptides may be determined using standard fluorescein filters (excitation=590 nm, emission=635 nm). The ratio of the activity at pH 5.6 to the activity at pH 8.0 is determined for the protease of the invention and for the reference protease of SEQ ID NO: 1 and the ratio of the protease of the invention relative to the ratio of the reference protease is calculated. Preferred proteases of the invention have such ratio relative to that of the reference protease of above 1, preferably of at least 1.05, at least 1.10, at least 1.15, at least 1.20, or at least 1.25. For more details, see Example 3.

The toxicity may be determined as in vitro toxicity on a human colon adenocarcinoma cell line such as HT-29 cells (e.g. DSMZ no. ACC 299). The cells are cultured in McCoy's 5A medium (e.g. from Cambrex) supplemented with 10% FBS (e.g. from Sigma, cat. no. F-6178), preferably at a density of $4 \cdot 10^4$ cells/well/200 µl in 96 well culture plates. After 24 hours of adaptation of the cells to the wells, proteases are added in serum-free medium (e.g. DMEM:F12, Invitrogen) supplemented with 0.5 g/l probumin (Millipore), 1% Insulin/transferrin/selenium supplement (e.g. from Invitrogen) and 1% penicillin and streptomycin (e.g. from Invitrogen) in 2-fold dilutions in triplicates in nine different concentrations (w/vol enzyme protein) and incubated another 24 hours. Viability is measured by metabolic capacity of the cells by using Alamar Blue (e.g. from Invitrogen) measurements.

The maximum metabolic activity (100%) is determined as the metabolic activity of the control (no protease added). For a given protease to be tested, its toxicity ratio is calculated as the concentration at which 50% of the maximum metabolic activity is obtained for this protease, divided by the concentration at which 50% of the maximum metabolic activity is obtained for the reference protease (SEQ ID NO: 1). For the proteases of the invention the toxicity ratio preferably is at least 1.1, preferably at least 1.2, preferably at least 1.3, preferably at least 1.4, preferably at least 1.5, preferably at least 1.6, preferably at least 1.7, preferably at least 1.8, preferably at least 1.9, most preferably at least 2.0. Toxicity ratio is explained in Example 6. Good correlation has been found for in vivo and in vitro toxicity results.

In still further particular embodiments, optionally, additional protease(s) may be used, for example a mammalian protease, for example in the form of pancreas extract from swine, or a microbial protease, for example derived from bacterial or fungal strains, such as *Bacillus, Pseudomonas, Aspergillus*, or *Rhizopus*. The protease may in particular be derived from a strain of *Aspergillus*, such as *Aspergillus oryzae* or *Aspergillus melleus*, in particular the product Prozyme 6™ (neutral, alkaline protease EC 3.4.21.63) which is commercially available from Amano Pharmaceuticals, Japan.

Cloning of Genes and Introducing Mutations

Standard procedures for cloning of genes and introducing mutations (random and/or site directed) may be used in order to obtain enzymes and enzyme variants such as the protease variants of the invention. The gene of interest (e.g. SEQ ID NO: 1 of WO 2005/035747 which is the gene encoding SEQ ID NO: 1 herein) may be amplified using primers designed to comprise restriction sites. For further description of suitable techniques reference is made to Sambrook et al. (1989), Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990, and WO 96/34946.

After digestion of the gene of interest and of the above plasmid using relevant restriction endonucleases for cloning purposes, the gene of interest and the plasmid can be joined in a ligation procedure involving ligase. After the ligase reaction the ligation mixture may be used to transform *E. coli* cells as described in Ausubel, F. M. et al. The transformed *E. coli* cells can be propagated in liquid media or on solid agar plates, plasmids can be rescued from the transformed cells and used to transform *B. subtilis* cells. Suitable competent *Bacillus* cells, such as MB1510, an 168-derivative (e.g. available from BGSC with accession no. 1A1 168 trpC2), may be transformed as described in WO 03/095658.

An *E. coli* plasmid-borne integration cassette for library construction may be used for *Bacillus* transformation. The method is described in detail in WO 03/095658. Alternatively, an in vitro amplified PCR-SOE-product (Melnikov and Youngman, Nucleic Acid Research 27, 1056) may be used.

The plasmid vector may contain the following elements:

i) a signal peptide coding region (e.g. obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA), followed by the pro-domain of the *Nocardiopsis* sp. protease of SEQ ID NO: 1 (residues 405-

899 of SEQ ID NO: 1 of WO 2005/035747) and the mature protease variant gene. This sequence may be preceded by and operably linked to:

ii) a DNA sequence comprising a mRNA stabilising segment (e.g. derived from the CryIIIa gene, as shown in WO 1999/043835);

iii) a marker gene (e.g. a chloramphenicol resistance gene); and iv) genomic DNA from *Bacillus subtilis* as 5' and 3' flanking segments upstream and downstream of the polynucleotide, respectively, to enable genomic integration by homologous recombination between the flanking segments and the *Bacillus* genome.

The protease of the invention may be used in combination with a lipase.

In the present context, a lipase means a carboxylic ester hydrolase EC 3.1.1.-, which includes activities such as EC 3.1.1.3 triacylglycerol lipase, EC 3.1.1.4 phospholipase A1, EC 3.1.1.5 lysophospholipase, EC 3.1.1.26 galactolipase, EC 3.1.1.32 phospholipase A1, EC 3.1.1.73 feruloyl esterase. In a particular embodiment, the lipase is an EC 3.1.1.3 triacylglycerol lipase.

In particular embodiments, the lipase is a mammalian lipase, for example in the form of pancreas extract from swine, or a microbial lipase, for example derived from bacterial or fungal strains, such as *Bacillus, Pseudomonas, Aspergillus*, or *Rhizopus*. The lipase may in particular be derived from a strain of *Rhizopus*, such as *Rhizopus javanicus, Rhizopus* oryzae, or *Rhizopus delemar*, for example the product Lipase D Amano 2000™ (also designated Lipase D2™) which is commercially available from Amano Pharmaceuticals, Japan.

In further particular embodiments, the lipase for use in the present invention is a recombinantly produced microbial lipase, for example derived from a fungus such as *Humicola* or *Rhizomucor*, from a yeast such as *Candida*, or from a bacterium such as *Pseudomonas*. In a preferred embodiment, the lipase is derived from a strain of *Humicola lanuginosa* or *Rhizomucor miehei*.

The *Humicola lanuginosa* (synonym *Thermomyces lanuginosus*) lipase is described in EP 305216, and particular lipase variants are described in, for example, WO 92/05249, WO 92/19726, WO 94/25577, WO 95/22615, WO 97/04079, WO 97/07202, WO 99/42566, WO 00/32758, WO 00/60063, WO 01/83770, WO 02/055679, WO 02/066622, and WO 2006/136159. Still further examples of fungal lipases are the cutinase from *Humicola insolens* which is described in EP 785994, and the phospholipase from *Fusarium oxysporum* which is described in EP 869167. Examples of yeast lipases are lipase A and B from *Candida antarctica* of which lipase A is described in EP 652945, and lipase B is described by, for example, Uppenberg et al in Structure, 2 (1994), 293. An example of a bacterial lipase is the lipase derived from *Pseudomonas cepacia*, which is described in EP 214761.

In a preferred embodiment, the lipase is at least 70% identical to the lipase of amino acids 1-269 of SEQ ID NO: 2 which is also described in WO 2006/136159. In additional preferred embodiments, the degree of identity to amino acids 1-269 of SEQ ID NO: 2 is at least 75%, at least 80%, at least 85%, at least 90%, at least 95%, or at least 99%. Lipases comprising, preferably having the following amino acid sequences are preferred: (i) amino acids +1 to +269 of SEQ ID NO: 2, (ii) amino acids −5 to +269 of SEQ ID NO: 2, (iii) amino acids −4 to +269 of SEQ ID NO: 2, (iv) amino acids −3 to +269 of SEQ ID NO: 2, (v) amino acids −2 to +269 of SEQ ID NO: 2; (vi) amino acids −1 to +269 of SEQ ID NO: 2, (vii) amino acids +2 to +269 of SEQ ID NO: 2, as well as (viii) any mixture of two or more of the lipases of (i)-(vii). In a particular embodiment, the lipase is selected from the lipases of (i), (ii), and any mixture of (i) and (ii). Preferred mixtures of (i) and (ii) comprise at least 5%, preferably at least 10%, 20%, 30%, 40%, 50%, 60%, 70%, 80%, 90%, or at least 95% of lipase (i), the percentages being determined by N-terminal sequencing using the Edman method, as described in Example 5 of WO 2006/136159. Other preferred mixtures are: (a) compositions comprising 35-75%, preferably 40-70%, more preferably 45-65% of lipase (ii); (b) compositions comprising 20-60%, preferably 25-55%, more preferably 30-50%, most preferably 35-47% of lipase (i); (c) compositions comprising up to 30%, preferably up to 25%, more preferably up to 20%, most preferably up to 16% of lipase (vii); and (d) any combination of (a), (b), and/or (c), such as a composition comprising 45-65% of lipase (ii), 35-47% of lipase (i), and up to 16% of lipase (vii).

In a still further preferred embodiment, the lipase, like the mammalian pancreatic lipase, is a 1,3-position specific lipase.

The protease of the invention, with or without a lipase as described above, may also be used in combination with an amylase.

In the present context, an amylase is an enzyme that catalyzes the endo-hydrolysis of starch and other linear and branched oligo- and polysaccharides. The amylose part of starch is rich in 1,4-alpha-glucosidic linkages, while the amylopectin part is more branched containing not only 1,4-alpha-but also 1,6-alpha-glucosidic linkages. In a particular embodiment, the amylase is an enzyme belonging to the EC 3.2.1.1 group.

In particular embodiments, the amylase is a mammalian amylase, for example in the form of pancreas extract from swine, or a microbial amylase, for example derived from bacterial or fungal strains, such as *Bacillus, Pseudomonas, Aspergillus*, or *Rhizopus*.

The amylase may in particular be derived from a strain of *Aspergillus*, such as *Aspergillus niger, Aspergillus oryzae* or *Aspergillus melleus*, for example either of the products Amylase A1™ derived from *Aspergillus oryzae* which is commercially available from Amano Pharmaceuticals, Japan, or Amylase EC™ derived from *Aspergillus melleus* which is commercially available from Extract-Chemie, Germany.

Other examples of fungal amylases are the *Aspergillus niger* amylase (SWISSPROT P56271), which is also described in Example 3 of WO 89/01969, and the *Aspergillus oryzae* amylase. Examples of variants of the *Aspergillus oryzae* amylase are described in WO 01/34784.

The alpha-amylase derived from *Bacillus licheniformis* is an example of a bacterial alpha-amylase. This amylase is, for example, described in WO 99/19467, together with other homologous bacterial alpha-amylases derived from, for example, *Bacillus amyloliquefaciens*, and *Bacillus stearothermophilus*, as well as variants thereof. Examples of additional amylase variants are those described in U.S. Pat. No. 4,933,279; EP 722490, EP 904360, and WO 2006/136161.

Preferred amylases are (i) an amylase comprising amino acids 1-481 of SEQ ID NO: 5 (such as amino acids 1-481, 1-484, or 1-486 thereof), amino acids 1-481 of SEQ ID NO: 3, and/or amino acids 1-483 of SEQ ID NO: 4. In a preferred embodiment, the amylase is an amylase having, or comprising, an amino acid sequence being, at least 70% identical to either of (i) amino acids 1-513 of SEQ ID NO: 5, (ii) amino acids 1-481 of SEQ ID NO: 3, and/or (iii) amino acids 1-483 of SEQ ID NO: 4. The amylases of SEQ ID NOs: 3-5 may, e.g., be prepared as described in WO 2006/136161. In additional preferred embodiments of either of (i), (ii), or (iii), the degrees of identity are at least 75%, at least 80%, at least 85%, at least 90%, at least 95%, or at least 99%.

Generally, the protease, lipase, and amylase enzymes (hereinafter "the enzyme(s)") for use according to the invention may be natural or wild type enzymes obtained from animals, in particular mammals, for example human or swine enzymes; from plants, or from microorganisms, but also any mutants, variants, fragments etc. thereof exhibiting the desired enzyme activity, as well as synthetic enzymes, such as shuffled enzymes, and consensus enzymes.

In a specific embodiment, the enzyme(s) are low-allergenic variants, designed to invoke a reduced immunological response when exposed to animals, including man. The term immunological response is to be understood as any reaction by the immune system of an animal exposed to the enzyme(s). One type of immunological response is an allergic response leading to increased levels of IgE in the exposed animal. Low-allergenic variants may be prepared using techniques known in the art. For example the enzyme(s) may be conjugated with polymer moieties shielding portions or epitopes of the enzyme(s) involved in an immunological response. Conjugation with polymers may involve in vitro chemical coupling of polymer to the enzyme(s), e.g. as described in WO 96/17929, WO 98/30682, WO 98/35026, and/or WO 99/00489. Conjugation may in addition or alternatively thereto involve in vivo coupling of polymers to the enzyme(s). Such conjugation may be achieved by genetic engineering of the nucleotide sequence encoding the enzyme(s), inserting consensus sequences encoding additional glycosylation sites in the enzyme(s) and expressing the enzyme(s) in a host capable of glycosylating the enzyme(s), see e.g. WO 00/26354. Another way of providing low-allergenic variants is genetic engineering of the nucleotide sequence encoding the enzyme(s) so as to cause the enzymes to self-oligomerize, effecting that enzyme monomers may shield the epitopes of other enzyme monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the enzyme(s) by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

In particular embodiments, the protease, lipase, and/or amylase enzymes are (i) stable at pH 4-8, preferably also at pH 3-4, more preferably at pH 3.5; (ii) active at pH 4-9, preferably 4-8, more preferably at pH 6.5; (iii) stable against degradation by pepsin and other digestive proteases (such as pancreas proteases, i.e., mainly trypsin and chymotrypsin); and/or (iv) stable and/or active in the presence of bile salts The term "in combination with" refers to the combined use according to the invention of the protease, lipase, and/or amylase. The combined use can be simultaneous, overlapping, or sequential, these three terms being generally interpreted in the light of the prescription made by the physician.

The term "simultaneous" refers to circumstances under which the enzymes are active at the same time, for example when they are administered at the same time as one or more separate pharmaceutical products, or if they are administered in one and the same pharmaceutical composition.

The term "sequential" refers to such instances where one and/or two of the enzymes are acting first, and the second and/or third enzyme subsequently. A sequential action can be obtained by administering the enzymes in question as separate pharmaceutical formulations with desired intervals, or as one pharmaceutical composition in which the enzymes in question are differently formulated (compartmentalized), for example with a view to obtaining a different release time, providing an improved product stability, or to optimizing the enzyme dosage.

The term "overlapping" refers to such instances where the enzyme activity periods are neither completely simultaneous nor completely sequential, viz. there is a certain period in which the enzymes are both, or all, active.

The term "a", for example when used in the context of the protease, lipase, and/or amylase of the invention, means at least one. In particular embodiments, "a" means "one or more," or "at least one", which again means one, two, three, four, five etc.

The relatedness between two amino acid sequences is described by the parameter "identity" which is described in detail above (in the protease section). The definition and procedure is applicable by analogy also to the lipases and amylases for use according to the invention.

The activity of the enzyme(s) of the invention can be measured using any suitable assay. Generally, assay-pH and assay-temperature are to be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C.

Examples of suitable enzyme (mainly protease) assays are included in Example 1 herein, as regards suitable lipase and amylase assays, reference is also made to WO 2006/136159 and WO 2006/136161, respectively.

Medicament

In the present context, the term "medicament" means a compound, or mixture of compounds, that treats, prevents and/or alleviates the symptoms of disease, preferably treats and/or alleviates the symptoms of disease. The medicament may be prescribed by a physician, or it may be an over-the-counter product.

Pharmaceutical Compositions

Isolation, purification, and concentration of the enzyme(s) of the invention may be carried out by conventional means. For example, they may be recovered from a fermentation broth by conventional procedures including, but not limited to, centrifugation, filtration, extraction, spray-drying, evaporation, or precipitation, and further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulphate precipitation), SDS-PAGE, or extraction (see, e.g., Protein Purification, J.-C. Janson and Lars Ryden, editors, VCH Publishers, New York, 1989).

For example, the lipase of SEQ ID NO: 2 may, e.g., be prepared on the basis of U.S. Pat. No. 5,869,438, viz. by recombinant expression in a suitable host cell of a DNA sequence which is a corresponding modification of SEQ ID NO: 1 of the US patent. Such modifications can be made by site-directed mutagenesis, as is known in the art.

In a particular embodiment, concentrated solid or liquid preparations of each of the enzyme(s) are prepared separately. These concentrates may also, at least in part, be separately formulated, as explained in more detail below.

In a further particular embodiment, the enzyme(s) are incorporated in the pharmaceutical compositions of the invention in the form of solid concentrates. The enzyme(s)

can be brought into the solid state by various methods as is known in the art. For example, the solid state can be either crystalline, where the enzyme molecules are arranged in a highly ordered form, or a precipitate, where the enzyme molecules are arranged in a less ordered, or disordered, form.

Crystallization may, for example, be carried out at a pH close to the pI of the enzyme(s) and at low conductivity, for example 10 mS/cm or less, as described in EP 691982. In a particular embodiment, the lipase for use according to the invention is a crystalline lipase, which can be prepared as described in Example 1 of EP 600868 B1. The lipase crystals may furthermore be cross-linked as described in WO 2006/044529.

Various precipitation methods are known in the art, including precipitation with salts, such as ammonium sulphate, and/or sodium sulphate; with organic solvents, such as ethanol, and/or isopropanol; or with polymers, such as PEG (Poly Ethylene Glycol). In the alternative, the enzyme(s) can be precipitated from a solution by removing the solvent (typically water) by various methods known in the art, e.g. lyophilization, evaporation (for example at reduced pressure), and/or spray drying.

In a further particular embodiment, the solid concentrate of the enzyme(s) has a content of active enzyme protein of at least 50% (w/w) by reference to the total protein content of the solid concentrate. In still further particular embodiments, the content of active enzyme protein, relative to the total protein content of the solid concentrate is at least 55, 60, 65, 70, 75, 80, 85, 90, or at least 95% (w/w). The protein content can be measured as is known in the art, for example by densitometer scanning of coomassie-stained SDS-PAGE gels, e.g. using a GS-800 calibrated densitometer from BIO-RAD; by using a commercial kit, such as Protein Assay ESL, order no. 1767003, which is commercially available from Roche; or on the basis of the method described in Example 8 of WO 01/58276.

Preferably, the enzyme protein constitutes at least 50%, more preferably at least 55, 60, 65, 70, 75, 80, 85, 90, 92, 94, 95, 96, or at least 97% of the protein spectrum of the solid enzyme concentrate for use according to the invention, as measured by densitometer scanning of a coomassie-stained SDS-PAGE gel. Such enzymes may be designated "isolated" enzymes or polypeptides.

A pharmaceutical composition of the invention comprises the enzyme(s), preferably in the form of concentrated enzyme preparations, more preferably solid concentrates, together with at least one pharmaceutically acceptable auxiliary, or subsidiary, material such as (i) at least one carrier and/or excipient; or (ii) at least one carrier, excipient, diluent, and/or adjuvant. Non-limiting examples of, optional, other ingredients, all pharmaceutically acceptable, are disintegrators, lubricants, buffering agents, moisturizing agents, preservatives, flavouring agents, solvents, solubilizing agents, suspending agents, emulsifiers, stabilizers, propellants, and vehicles.

Generally, depending i.a. on the medical indication in question, the composition of the invention may be designed for all manners of administration known in the art, preferably including enteral administration (through the alimentary canal). Thus, the composition may be in solid, semi-solid, liquid, or gaseous form, such as tablets, capsules, powders, granules, microspheres, ointments, creams, foams, solutions, suppositories, injections, inhalants, gels, lotions, and aerosols. The medical practitioner will know to select the most suitable route of administration and of course avoid potentially dangerous or otherwise disadvantageous administration routes.

The following methods and auxiliary materials are therefore also merely exemplary and are in no way limiting.

For solid oral preparations, the enzyme(s) can be used alone or in combination with appropriate additives to make pellets, micropellets, tablets, microtablets, powders, granules or capsules, for example, with conventional carriers, such as lactose, mannitol, corn starch, or potato starch; with excipients or binders, such as crystalline, or microcrystalline, cellulose, cellulose derivatives, acacia, corn starch, or gelatins; with disintegrators, such as corn starch, potato starch, or sodium carboxymethylcellulose; with lubricants, such as carnauba wax, white wax, shellac, waterless colloid silica, polyethylene glycol (PEGs, also known under the term macrogol) from 1500 to 20000, in particular PEG 4000, PEG 6000, PEG 8000, povidone, talc, monolein, or magnesium stearate; and if desired, with diluents, adjuvants, buffering agents, moistening agents, preservatives such as methylparahydroxybenzoate (E218), colouring agents such as titanium dioxide (E171), and flavouring agents such as saccharose, saccharin, orange oil, lemon oil, and vanillin. Oral preparations are examples of preferred preparations for treatment of the medical indication of PEI.

The enzyme(s) can also, quite generally, be formulated into liquid oral preparations, by dissolving, suspending, or emulsifying them in an aqueous solvent such as water, or in non-aqueous solvents such as vegetable or other similar oils, synthetic aliphatic acid glycerides, esters of higher aliphatic acids, propylene glycol, polyethylene glycol such as PEG 4000, or lower alcohols such as linear or ramified C1-C4 alcohols, for example 2-propanol; and if desired, with conventional subsidiary materials or additives such as solubilizers, adjuvants, diluents, isotonic agents, suspending agents, emulsifying agents, stabilizers, and preservatives.

The use of liposomes as a delivery vehicle is another method of possible general interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will normally be neutral or acidic lipids, such as cholesterol, phosphatidyl serine, phosphatidyl glycerol, and the like. For preparing the liposomes, the procedure described by Kato et al. (1991) J. Biol. Chem. 266:3361 may be used.

Unit dosage forms for oral or rectal administration such as syrups, elixirs, powders, and suspensions may be provided wherein each dosage unit, for example, teaspoonful, tablespoonful, capsule, tablet or suppository, contains a predetermined amount of the enzyme(s). Similarly, unit dosage forms for injection or intravenous administration may comprise the enzyme(s) in a composition as a solution in sterile water, normal saline, or another pharmaceutically acceptable carrier.

The term "unit dosage form", as used herein, refers to physically discrete units suitable as unitary dosages for human and animal subjects, each unit containing a predetermined quantity of enzyme(s) in an amount sufficient to produce the desired effect.

In a particular embodiment, the pharmaceutical composition of the invention is for enteral, preferably oral, administration.

In further particular embodiments, the oral composition is (i) a liquid composition containing crystals of the enzyme(s); (ii) a liquid suspension of sediments of (highly) purified enzyme(s); (iii) a gel containing the enzyme(s) in solid or solubilized form; (iv) a liquid suspension of immobilized enzyme(s) or of enzymes adsorbed to particles and the like; or (v) a solid composition in the form of enzyme(s)-containing powder, pellets, granules, or microspheres, if desired in the form of tablets, capsules, or the like, that are optionally coated, for example with an acid-stable coating.

In another particular embodiment of the composition, the enzyme(s) are compartmentalized, viz. separated from each other, for example by means of separate coatings.

In a still further particular embodiment of the composition, the protease is separated from other enzyme components of the composition, such as the lipase, and/or the amylase.

The dosage of the enzyme(s) will vary widely, depending on the specific enzyme(s) to be administered, the frequency of administration, the manner of administration, the severity of the symptoms, and the susceptibility of the subject to side effects, and the like. Some of the specific enzymes may be more potent than others.

Examples of solid oral preparations of the enzyme(s) of the invention comprise: (i) a protease having SEQ ID NO: 6, 7, 8, 9, 10, or 11; (ii) a lipase having at least 70% identity to amino acids 1-269 of SEQ ID NO: 2; and/or (iii) an amylase having at least 70% identity to an amylase selected from the group consisting of a) an amylase having amino acids 1-513 of SEQ ID NO: 5, b) an amylase having amino acids 1-481 of SEQ ID NO: 3, and c) an amylase having amino acids 1-483 of SEQ ID NO: 4. In a more preferred solid oral preparation of the invention, (ii) the lipase comprises amino acids 1-269 of SEQ ID NO: 2, and (iii) the amylase comprises amino acids 1-486 of SEQ ID NO: 5.

Examples of anticipated daily clinical dosages of the enzymes of (i), (ii), and (iii) are as follows (all in mg enzyme protein per kg of bodyweight (bw)): For the protease of (i): 0.005-500, 0.01-250, 0.05-100, or 0.1-50 mg/kg bw; for the lipase of (ii): 0.01-1000, 0.05-500, 0.1-250, or 0.5-100 mg/kg bw; for the amylase of (iii): 0.001-250, 0.005-100, 0.01-50, or 0.05-10 mg/kg bw, preferably for the protease of (i): 0.05-100, 0.1-50, or 0.5-25 mg/kg bw; for the lipase of (ii): 0.1-250, 0.5-100, or 1-50 mg/kg bw; and for the amylase of (iii): 0.01-50, 0.05-10, or 0.1-5 mg/kg bw.

The amide (peptide) bonds, as well as the amino and carboxy termini, may be modified for greater stability on oral administration. For example, the carboxy terminus may be amidated.

Particular embodiments of pharmaceutical compositions of the invention, suitable for the treatment of digestive disorders, PEI, pancreatitis, cystic fibrosis, diabetes type I, and/or diabetes type II, may be prepared by incorporating the enzyme(s) of the invention into pellets. The pellets may generally comprise from 10-90% (w/w, relative to the dry weight of the resulting pellets) of a physiologically acceptable organic polymer, from 10-90% (w/w, relative to the dry weight of the resulting pellets) of cellulose or a cellulose derivative, and from 80-20% (w/w, relative to the dry weight of the resulting pellets) of the enzyme(s), the total amount of organic polymer, cellulose or cellulose derivative and enzyme(s) making up to 100% in each case.

The physiologically acceptable organic polymer can be selected from the group comprising polyethylene glycol 1500, polyethylene glycol 2000, polyethylene glycol 3000, polyethylene glycol 4000, polyethylene glycol 6000, polyethylene glycol 8000, polyethylene glycol 10000, polyethylene glycol 20000, hydroxypropyl methylcellulose, polyoxyethylene, copolymers of polyoxyethylene-polyoxypropylene and mixtures of said organic polymers. Polyethylene glycol 4000 is preferred as physiologically acceptable organic polymer.

The cellulose or a cellulose derivative can e.g. be selected from cellulose, cellulose acetate, cellulose fatty acid ester, cellulose nitrates, cellulose ether, carboxymethyl cellulose, ethyl cellulose, hydroxyethyl cellulose, hydroxypropyl cellulose, methyl cellulose, methyl ethylcellulose and methylhydroxypropyl cellulose. Cellulose, in particular microcrystalline cellulose is preferred as cellulose or cellulose derivative.

The resulting pellets may be coated with a suitable enteric coating, other non-functional coating or be used directly without such coating. Further, the resulting pellets may be filled in capsules like hard gelatin capsules or gelatin free capsules of a suitable size for therapy of a disorder or disease as described in more detail above. In an embodiment of the invention, pellets produced from different enzyme types, in particular from lipase, protease and/or amylase may be filled into said capsules. While filling the capsules with the different enzyme types, the dosing of the single enzyme types (viz. lipase, protease or amylase) may be adapted to specific needs of a certain indication group or a certain patient subgroup by adding a specified amount of any of lipase, protease and/or amylase to the capsules, i.e. capsules may be produced which vary in their specific ratios of lipase:protease:amylase.

Preferred pharmaceutical compositions of the protease of the invention are described in WO 2005/092370, in particular formulations comprising the preferred excipients mentioned therein. In a particularly preferred embodiment, the pharmaceutical composition comprises a macrogolglyceride mixture of mono-, di- and tri-acylglycerides and polyethylene glycol (PEG) mono- and di-esters of aliphatic C6-C22 carboxylic acids, and also possibly small proportions of glycerol and free polyethylene glycol.

The polyethylene glycol (PEG) contained in the macrogolglyceride mixtures is preferably PEG which has on average 6 to at most 40 ethylene oxide units per molecule or a molecular weight of between 200 and 2000.

One further aspect of the invention provides for the pharmaceutical composition of the enzyme(s) of the invention to comprise a system consisting of surfactant, co-surfactant and lipophilic phase, the system having an HLB value (Hydrophilic-Lipophilic Balance) greater than or equal to 10 and a melting point greater than or equal to 30° C. In a preferred embodiment, the system has an HLB value of 10 to 16, preferably of 12 to 15, and has a melting point of between 30 and 600° C., preferably between 40 and 500° C. In particular, the system characterised by HLB value and melting point is a mixture of mono-, di- and triacylgylcerides and mono- and diesters of polyethylene glycol (PEG) with aliphatic carboxylic acids with 8 to 20, preferably 8 to 18, carbon atoms, whereby the polyethylene glycol preferably has about 6 to about 32 ethylene oxide units per molecule, and the system optionally contains free glycerin and/or free polyethylene glycol. The HLB value of such a system is preferably regulated by the chain length of the PEG. The melting point of such a system is regulated by the chain length of the fatty acids, the chain length of the PEG and the degree of saturation of the fatty-acid chains, and hence the starting oil for the preparation of the macrogolglyceride mixture.

"Aliphatic C8-C18 carboxylic acids" designates mixtures in which caprylic acid (C8), capric acid (C10), lauric acid (C12), myristic acid (C14), palmitic acid (C16) and stearic acid (C18) are contained in a significant and variable proportion, if these acids are saturated, and the corresponding unsaturated C8-C18 carboxylic acids. The proportions of these fatty acids may vary according to the starting oils.

Such a mixture of mono-, di- and triacylgylcerides and mono- and diesters of polyethylene glycol (PEG) with aliphatic carboxylic acids with 8 to 18 carbon atoms can for example be obtained by a reaction between a polyethylene glycol with a molecular weight of between 200 and 1500 and a starting oil, the starting oil consisting of a triglyceride mixture with fatty acids which are selected from the group comprising caprylic acid, capric acid, lauric acid, myristic acid, palmitic acid, stearic acid, oleic acid and linolenic acid, individually or as a mixture. Optionally, the product of such a reaction may also contain small proportions of glycerin and free polyethylene glycol.

Such mixtures are commercially available for example under the trade name Gelucire®. One advantageous embodiment of the invention provides that, of the products known under the trade name Gelucire®, in particular "Gelucire® 50/13" and/or "Gelucire® 44/14" represent suitable mixtures for use in the pharmaceutical preparations according to the invention.

Gelucire® 50/13 is a mixture with mono-, di- and triacylglycerides and mono- and diesters of polyethylene glycol, with palmitic acid (C16) and stearic acid (C18) at 40% to 50% and 48% to 58%, respectively making up the major proportion of bound fatty acids. The proportion of caprylic acid (C8) and capric acid (C10) is less than 3% in each case, and the proportion of lauric acid (C12) and myristic acid (C14) in each case is less than 5%.

Gelucire® 44/14 is a mixture with mono-, di- and triacylgylcerides and mono- and diesters of polyethylene glycol, the respective proportions of palmitic acid (C16) being 4 to 25%, stearic acid (C18) 5 to 35%, caprylic acid (C8) less than 15%, capric acid (C10) less than 12%, lauric acid (C12) 30 to 50% and myristic acid (C14) 5 to 25%. Gelucire® 44/14 can for example be prepared by an alcoholysis/esterification reaction using palm kernel oil and polyethylene glycol 1500.

A preferred embodiment of the present invention provides for a pharmaceutical composition of the enzyme(s) of the invention which comprises a system containing a mixture of mono-, di- and triacyl-glycerides and polyethylene glycol mono- and diesters of aliphatic C8-C18 carboxylic acids and also possibly small proportions of glycerin and free polyethylene glycol, the system having a melting point between 40° C. and 55° C. and an HLB value in the range between 12 and 15. More preferred, the system has a melting point between 44° C. and 50° C. and an HLB value in the range from 13-14. Alternatively, the system has a melting point around 44° C. and an HLB value of 14, or the system has a melting point around 50° C. and an HLB value of 13.

Methods of Treatment

The protease for use according to the invention, optionally in combination with a lipase, and/or an amylase (the enzyme(s) of the invention), is useful in the therapeutic, and/or prophylactic, treatment of various diseases or disorders in animals. The term "animal" includes all animals, and in particular human beings. Examples of animals are non-ruminants, and ruminants, such as sheep, goat, and cattle, e.g. beef cattle, and cow. In a particular embodiment, the animal is a non-ruminant animal. Non-ruminant animals include monogastric animals, e.g. horse, pig (including, but not limited to, piglets, growing pigs, and sows); poultry such as turkey, duck and chicken (including but not limited to broiler chicks, layers); young calves; pets such as cat, and dog; and fish (including but not limited to salmon, trout, tilapia, catfish and carps; and crustaceans (including but not limited to shrimps and prawns). In a particular embodiment the animal is a mammal, more in particular a human being.

For example, the enzyme(s) are useful in the treatment of digestive disorders like maldigestion or dyspepsia that are often caused by a deficient production and/or secretion into the gastrointestinal tract of digestive enzymes normally secreted from, the stomach, and the pancreas.

Further, the enzyme(s) are particularly useful in the treatment of PEI. PEI can be verified using, i.a., the Borgström test (JOP. J Pancreas (Online) 2002; 3(5):116-125), and it may be caused by diseases and conditions such as pancreatic cancer, pancreatic and/or gastric surgery, e.g. total or partial resection of the pancreas, gastrectomy, post gastrointestinal bypass surgery (e.g. Billroth II gastroenterostomy); chronic pancreatitis; tropical pancreatitis; hereditary pancreatitis; Shwachman Diamond Syndrome; ductal obstruction of the pancreas or common bile duct (e.g. from neoplasm); and/or cystic fibrosis (an inherited disease in which a thick mucus blocks the ducts of the pancreas). The enzyme(s) may also be useful in the treatment of acute pancreatitis.

The effect of the enzyme(s) on digestive disorders can be measured as generally described in EP 0600868, in which Example 2 describes an in vitro digestibility test for measuring lipase stability under gastric conditions, and Example 3 an in vitro digestibility test for lipase activity in the presence of bile salts. Corresponding tests can be set up for the protease and amylase. Also WO 02/060474 discloses suitable tests, for example (1) an in vitro test for measuring lipid digestion in a swine test feed, and (2) an in vivo trial with pancreas insufficient swine in which the digestibility of fat, protein and starch is measured.

In a particular embodiment, the effect of the protease of the invention is measured using the in vivo screening test of Example 4.

As another example, the enzyme(s) are useful in the treatment of Diabetes mellitus type I, and/or type II, in particular for adjuvant treatment in a diabetes therapy of digestive disorders usually accompanying this disease, with a view to diminishing late complications.

The effect on Diabetes mellitus of the enzyme(s) may be determined by one or more of the methods described in WO 00/54799, for example by controlling the level of glycosylated haemoglobin, the blood glucose level, hypoglycaemic attacks, the status of fat-soluble vitamins like vitamins A, D and E, the required daily dosage of insulin, the body-weight index, and hyper glycaemic periods.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Chemicals used were commercial products of at least reagent grade.

Example 1

Enzyme Assays

Assays for lipase, protease and amylase activity of porcine pancreatin have been published by the FIP (Fédération Internationale Pharmaceutique) as well as the European Pharmacopoeia and the United States Pharmacopeia. 1 FIP-unit=1 Ph.Eur.-unit (European Pharmacopoeia). The assays are described in, e.g.: Fédération Internationale Pharmaceutique, Scientific Section: International Commission for the standardisation of pharmaceutical enzymes. a) "Pharmaceutical Enzymes," Editors: R. Ruyssen and A. Lauwers, E. Story Scientia, Ghent, Belgium (1978), b) European Pharmacopoeia. See also Deemester et al in Lauwers A, Scharpé S (eds.): Pharmaceutical Enzymes, New York, Marcel Dekker, 1997, p. 343-385. Appropriate enzyme standards can be procured from: International Commission on Pharmaceutical Enzymes, Centre for Standards, Harelbekestraat 72, B-9000 Ghent.

The protease FIP assay as well as other suitable assays for protease, lipase and amylase are described below.

Protease FIP Assay

Protease activity may be determined using a FIP assay (Fédération Internationale Pharmaceutique), 1 FIP-unit=1 Ph.Eur.-unit (European Pharmacopoeia). This assay is described, together with other FIP assays in: Federation Internationale Pharmaceutique, Scientific Section International Commission for the standardisation of pharmaceutical enzymes. a) "Pharmaceutical Enzymes," Editors: R. Ruyssen and A. Lauwers, E. Story Scientia, Ghent, Belgium (1978), b) European Pharmacopoeia. See also Deemester et at in Lauwers A, Scharpé S (eds.): Pharmaceutical Enzymes, New York, Marcel Dekker, 1997, p. 343-385.

This assay was used for determining protease activity in pancreatin. For determining FIP activity of microbial proteases, the activation step by adding enterokinase was omitted.

Principle: The substrate casein is hydrolysed by protease at pH 7.5 and at a temperature of 35° C. The reaction is stopped by addition of trichloroacetic acid, and non-degraded casein is filtered off. The quantity of peptides remaining in solution is determined by spectrophotometry at 275 nm.

Definition of the activity: The protease activity is determined as the quantity of peptides not precipitated by a 5.0% (wt/vol, i.e. 5.0 g/100 ml) solution of trichloroacetic acid, by reference to a pancreas reference powder (protease reference standard) of known FIP activity.

Materials and Methods:

Casein Solution:

1.25 g casein (dry matter), e.g. Calbiochem no. 218680, is suspended in water until a practically clear solution is obtained. pH is adjusted to 8.0, and the solution is diluted with water to a final volume of 100 ml. Here and in the following, water means deionized water.

Borate Buffer pH 7.5:

2.5 g sodium chloride, 2.85 g disodium tetraborate and 10.5 g boric acid are dissolved in 900 ml water, pH is adjusted to pH 7.5+/−0.1 and diluted to 1000 ml with water.

Filter Paper:

Folded filters with a diameter of 125 mm, e.g. Schleicher & Schuell no. 1573½. Test of filter paper: Filter 5 ml of 5.0% trichloro acetic acid through the filter. The absorption at 275 nm of the filtrate should be less than 0.04, using unfiltered trichloroacetic acid solution as a blank.

Protease Reference Standard:

Protease (pancreas) commercially available from the International Commission on Pharmaceutical Enzymes, Centre for Standards, Harelbekestraat 72, B-9000 Ghent, Belgium. The standard has a labelled activity (A) in FIP/Ph.Eur.-units/g. Accurately weigh a quantity corresponding to approx. 130 protease-FIP/Ph.Eur.-units. Add a spatula tip of sea sand, wet with a few drops of ice-cold 0.02M calcium chloride (pH 6.0-6.2), and triturate the whole with a flat-ended glass rod. Dilute with approx. 90 ml of the same ice-cold calcium chloride solution and stir the suspension for 15 to 30 minutes in an ice-bath. pH is adjusted to 6.1 and the volume is adjusted to 100 ml with the same calcium chloride solution. 5.0 ml of this suspension is diluted with borate buffer pH 7.5 to 100 ml. For the activity test, 1.0, 2.0 and 3.0 ml of this solution is used as reference (in what follows designated S1, S2, and S3, S for Standard).

Test Suspension:

Prepare a suspension of the sample as described above for the protease reference standard, using a sample amount equivalent to approx. 260 FIP/Ph.Eur.-units. pH is adjusted to 6.1 and water is added to 100 ml. 5.0 ml of this solution is mixed with 5 ml of calcium chloride solution. 5 ml of this dilution is further diluted to 100 ml with borate buffer. Use 2.0 ml of this solution for the assay (in what follows the sample is designated Un, sample of unknown activity, number n).

Assay Procedure (Activity Test):

The assay is performed for the three reference suspensions (S1, S2, S3) and for the sample suspension (Un), all in triplicate. One blank per sample is sufficient (designated S1 b, S2b, S3b, and Unb, respectively). A blind (B) is prepared without sample/standard as compensation liquid for the spectrophotometer. Borate buffer is added to tubes as follows: Blind (B) 3.0 ml; sample (Un) 1.0 ml; standards (S1, S2 and S3) 2.0, 1.0 and 0 ml, respectively. Protease reference standard is added to S1, S2 and S3 as follows: 1.0, 2.0, and 3.0 ml, respectively. The test suspension is added to the sample tubes as follows (Un): 2.0 ml. 5 ml trichloro acetic acid is added to all blinds (S1b, S2b, S3b, Un and B) followed by immediate mixing. All tubes are stopped with a glass stopper and placed together with the substrate solution in a water-bath at constant temperature (35+/−0.5° C.). When temperature equilibration is reached, at time zero, 2.0 ml casein solution is added to tubes S1, S2, S3 and Un, followed by immediate mixing. Exactly 30 minutes after, 5.0 ml trichloro acetic acid is added to each of tubes S1, S2, S3 and Un, followed by immediate mixing. The tubes are withdrawn from the water bath and allowed to stand at room temperature for 20 minutes to complete the precipitation of the proteins. The content of each tube is filtered twice through the same filter, and the absorption of the filtrates is measured at 275 nm using the filtrate from tube B as compensation liquid. The activity of the sample (Un) in FIP units is calculated relative to the known labelled activity (A) of the standards (S1, S2, S3). The absorption values minus the respective blinds (e.g. the absorption of S1 minus the absorption of S1b) should lie in the interval of 0.15-0.60.

Protease Protazyme AK Assay

Substrate: 1 Protazyme AK tablet (Megazyme T-PRAK1000) suspended in 2.0 ml 0.01% Triton X-100. A homogeneous suspension was prepared by stirring Temperature: 37° C.

Assay buffer: 100 mM HEPES/NaOH, 0.01% Triton X-100, pH 7.0

500ul (micro liter) Protazyme AK substrate suspension and 500 ul Assay buffer were mixed in an Eppendorf tube and placed on ice. 20ul protease sample (diluted in 0.01% Triton X-100) was added. The assay was initiated by transferring the Eppendorf tube to an Eppendorf thermomixer, which was set to 37° C. The tube was incubated for 15 minutes on the Eppendorf thermomixer at its highest shaking rate (1400 rpm). The incubation was stopped by transferring the tube back to the ice bath. After a few minutes the tube was centrifuged in an cold centrifuge (15000 rpm, 3 min). 200ul supernatant was transferred to a microtiter plate. $OD_{650}$ was read as a measure of protease activity. A buffer blind was included in the assay (instead of enzyme).

Protease Suc-AAPF-pNA Assay

Substrate: Suc-AAPF-pNA (Sigma® S-7388).

Assay buffer: 100 mM succinic acid, 100 mM HEPES, 100 mM CHES, 100 mM CABS, 1 mM $CaCl_2$, 150 mM KCl, 0.01% Triton® X-100 adjusted to pH 9.0 with HCl or NaOH.

Assay temperature: 25° C.

300 µl diluted protease sample was mixed with 1.5 ml of the assay buffer and the activity reaction was started by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer as a measurement of the protease activity. The protease samples were diluted prior to the activity measurement in order to ensure that all activity measurements fell within the linear part of the dose-response curve for the assay.

Lipase

Substrate: para-Nitro-Phenyl (pNP) Valerate

Assay pH: 7.7

Assay temperature: 40° C.

Reaction time: 25 min

The digested product with yellow colour has a characteristic absorbance at 405 nm. Its quantity is determined by spectrophotometry. The lipase activity may be determined relative to an enzyme standard of known activity. The activity may be expressed in Lipolase Units (LU). One LU (Lipolase Unit) is the amount of enzyme which releases 1 mmol titratable butyric acid per minute under the above standard conditions. 1 KLU=1000 LU.

Amylase

Substrate: Phadebas tablets (Pharmacia Diagnostics; cross-linked, insoluble, blue-coloured starch polymer, which is mixed with bovine serum albumin and a buffer substance, and manufactured into tablets)

Assay Temperature: 37° C.

Assay pH: 4.3

Reaction time: 20 min

After suspension in water the starch is hydrolyzed by the alpha-amylase, giving soluble blue fragments. The absorbance of the resulting blue solution, measured at 620 nm, is a function of the alpha-amylase activity. One Fungal alpha-Amylase Unit (1 FAU) is the amount of enzyme which breaks down 5.26 g starch (Merck, Amylum solubile Erg. B. 6, Batch 9947275) per hour at the standard assay conditions.

Example 2

Preparation of Proteases

The protease variants of SEQ ID NO: 6, 7, 8, 9, 10, and 11 were prepared by standard procedures, in brief: Introducing random and/or site-directed mutations into the gene, transforming Bacillus subtilis host cells with the mutated genes, fermenting the transformed host cells (e.g. as described in Example 1 of WO 2004/111220), and purifying the protease from the fermentation broth. The reference protease (SEQ ID NO: 1) was produced recombinantly in Bacillus subtilis in a similar manner.

For purifying larger amounts of protease, the culture broth was centrifuged (13.000 rpm. for 20 min) to give a clear supernatant and the supernatant was filtered through a 0.45 µm filter to remove the rest of the Bacillus host cells. The pH of the filtrate was adjusted to pH 9.0 with 3M Tris and the protease solution was applied to a MEP Hypercel column (PALL Life Sciences) equilibrated in 50 mM Tris/HCl, pH 9.0. After washing the column with several column volumes of the equilibration buffer, the protease was eluted with 50 mM $CH_3COOH$/NaOH, pH 4.0. Fractions, collected during elution, were tested for protease activity (using the End-point Protazyme AK assay of Example 1). Active fractions were pooled, pH was adjusted to pH 4.5 and the pool was diluted with deionised water to give the same conductivity as 20 mM $CH_3COOH$/NaOH, 50 mM $H_3BO_3$, 1 mM $CaCl_2$, pH 4.5 (SP equilibration buffer). The adjusted pool was applied to a SP sepharose HP column equilibrated in SP equilibration buffer. After washing the column with several column volumes of the SP equilibration buffer, the column was eluted over 5 column volumes with a linear NaCl gradient (0→0.5M) in the same buffer. Fractions, collected during elution, were tested for protease activity (using Protazyme AK assay). Active fractions from the column were pooled as the purified protease product.

For preparing smaller amounts of protease (micropurification), the culture broth was sterile filtered through a 0.45 µm filter. To each well of a filter plate (Whatman, Unifilter 800 µl, 25-30 µm MBPP) about 100 µl MEP-HyperCel chromatographic medium slurry was added. The chromatographic medium was washed twice with 200 µl 25 mM Tris, 25 mM sodium borate, 2 mM $CaCl_2$, pH 8.5 by incubating 5 min at room temperature with vigorous shaking (Heidolph, Titramax 101, 1000 rpm) to stir up the chromatographic medium and subsequent removal of liquid by vacuum (Whatman, UniVac 3). Then 100 µl binding buffer (0.5 M Tris, 25 mM sodium borate, 10 mM $CaCl_2$, pH 8.5) and 400 µl culture supernatant was transferred to the wells of the filter plate. Four wells were normally micropurified for each protease. To bind the protease to the chromatographic medium, the filter plate was incubated 30 min with vigorous shaking. After removing unbound material by vacuum, the binding step was repeated: 100 µl binding buffer and 400 µl culture supernatant was added, incubated 30 min with shaking and unbound material removed by vacuum. The MEP-HyperCel medium was then washed once with 0.1 M Tris, 25 mM sodium borate, 2 mM $CaCl_2$, pH 8.5, once with 25 mM Tris, 25 mM sodium borate, 2 mM $CaCl_2$, pH 8.5 and once with 10 mM Tris, 25 mM sodium borate, 2 mM $CaCl_2$, pH 8.5. In each washing step 200 µl buffer was added, the plate was incubated under vigorous shaking for 10 min at room temperature and the buffer was removed by vacuum. To liberate the protease from the chromatographic medium, 100 µl elution buffer (50 mM sodium acetate, 2 mM $CaCl_2$, pH 4.3) was added and the filter plate was incubated at room temperature with vigorous shaking for 10 min. Elution buffer containing the protease was transferred by vacuum to a 96 well plate. The elution step was repeated by adding 100 µl elution buffer, shaking for 10 min at room temperature and collecting in the same 96 well plate. The pooled micropurified proteases were stored at −18° C.

The enzyme protein concentration was determined by active site titration as described below, or calculated on the basis of the $A_{280}$ values and the amino acid sequence (amino acid composition), using the principles outlined in S. C. Gill & P. H. von Hippel, Analytical Biochemistry 182, 319-326, (1989). Enzyme protein concentration may also be determined by amino acid analysis, e.g. as described in Example 3 of WO 2004/111221.

The determination of enzyme concentration by active site titration was made using the tight binding barley chymotrypsin inhibitor 2A (Cl-2A; see Ludvigsen, S., Shen, H. Y., Kjaer, M., Madsen, J. C., Poulsen, F. M.: Refinement of the three-dimensional solution structure of barley serine proteinase inhibitor 2 and comparison with the structures in crystals. J. Mol. Biol., vol 222, pp. 621-635, 1991) as follows. In a microtiter plate 20 µl aliquots of micropurified protease (appropriately diluted with 0.1 M Tris, 0.0225% Brij 35 (Polyoxyethylene(23)lauryl ether), pH 8.6) was mixed with 20 µl Cl-2A (normally diluted to 2, 1.5, 1, 0.5, 0.25, 0.125 0.0625 and 0 µM with 0.1 M Tris, 0.0225% Brij 35, pH 8.6). After 1 hour incubation with shaking, residual activity was measured by adding 160 µl substrate solution (normally 0.4 mg/ml Suc-Ala-Ala-Ala-pNA in 0.1 M Tris, 0.0225% Brij 35, pH 8.6 made from stock of 200 mg/ml in DMSO) and measuring absorbance at 405 nm every 10 s for 3 min (Spectramax, Molecular Devices). Active protease concentration was calculated from linear regression of residual activity versus inhibitor concentration of wells with (significant) residual activity.

Table 1 is a list of selected variants of the invention. These proteases were tested as described in the following examples.

TABLE 1

List of variants

| Variant | SEQ ID NO: | Mutations |
|---|---|---|
| Reference protease | 1 | — |
| VAR294 | 6 | E125D |
| VAR295 | 7 | R38T |
| VAR375 | 8 | T44K + S99P |
| VAR213 | 9 | S69T |
| VAR307 | 10 | R165S |
| VAR203 | 11 | S69T + E125D |

Example 3

Proteases with Improved pH-Ratio

Protease variant VAR294 (SEQ ID NO: 6) was tested for protease activity at pH 5.6 and pH 8.0 and compared as described below to the corresponding activity of the reference protease (SEQ ID NO: 1).
Protease Assay The EnzChek® Protease Assay Kit from Molecular Probes (Invitrogen, catalogue number E6639) was used. As substrate it uses casein derivatives that are heavily labelled with the pH-insensitive red-fluorescent BODIPY® TR-X dyes, resulting in almost total quenching of the conjugate's fluorescence. Protease-catalyzed hydrolysis releases highly fluorescent BODIPY TR-X dye-labelled peptides. The accompanying increase in fluorescence is proportional to protease activity.
Reagents:

One tube of EnzChek Protease Assay Kit for red fluorescence (200 µg) is solubilized in 200 µl 0.1 M $NaHCO_3$ (pH 8) to give a stock solution of 1 mg/mL.

Assay buffer pH 8 is prepared by adjusting 100 mM Tris/base to pH 8.0 with HCl. 6.25 µg/ml labelled substrate is added.

Assay buffer pH 5.6 is prepared by mixing 25 ml 0.2 M succinic acid with 37.5 ml 0.2 M NaOH (Ref.:Gomori, Meth. Enzymol. 1, 141 (1955)). To compensate for the added protease, 1.143 ml 1M HCl is added for each 100 ml of assay buffer. Thereby, the pH of the buffer is lowered to about 5.0. 5 µg/ml labelled substrate is added.
Sample Analysis:

10 µl of 0.5 µM protease solution (reference protease, protease variant, all in duplicates) is mixed with 40 µl of the respective buffer in a 384-well plate. Incubation for 60 minutes at room temperature; vigorous shaking at 750 rpm/min. The fluorescence is read in a fluorescence micro plate reader at t=0 and t=60 min. BODIPY TR-X labelled peptides have excitation/emission maxima of 589/617 nm. The standard fluorescein filters (excitation=590 nm, emission=635 nm) were used to detect BODIPY TR-X dye-labelled peptides.
Calculation:

The read-out at pH5.6 at t=60 min has to be 4 times higher as compared to t=0. The ratio between the read-out at pH5.6 and the read out at pH8 is calculated. The resulting number has to be 1.4 times higher than the respective number of the reference enzyme. The ratio for the variant is compared to the average ratio of 8 reference wells on each 96-well plate. For the calculation, t=0 is subtracted from t=60 at both pH-values.
Results The variant listed in Table 2 below has a different activity ratio at pH 5.6/pH 8.0 as compared to the reference protease which has a pH5.6/pH8 ratio of 1.00.

TABLE 2

| Variant | SEQ ID NO: | pH 5.6/pH 8 activity ratio |
|---|---|---|
| VAR294 | 6 | 1.27 |

Example 4

In Vivo Screening Test for Protease Efficacy

Purified protease variants VAR294, VAR295, VAR375, VAR213, and VAR307 (SEQ ID NO: 6, 7, 8, 9, and 10) were studied in a protease screening test in groups of 3-4 female Göttingen minipigs (Ellegaard) with induced Pancreatic Exocrine Insufficiency (PEI). Pancreatic Exocrine Insufficiency (PEI) was induced in the minipigs by ligation of the pancreatic duct, and they were also fitted with an ileo-caecal re-entrant cannula, all under isofluorane anaesthesia and at a weight of about 25 kg, as otherwise described in Tabeling et al. (Tabeling et al. (1999): "Studies on nutrient digestibilities (pre-caecal and total) in pancreatic duct-ligated pigs and the effects of enzyme substitution", J. Anim. Physiol. A. Anim. Nutr. 82: 251-263) and in Gregory et al. (Gregory et al. (1999): "Growth and digestion in pancreatic duct ligated pigs, Effect of enzyme supplementation" in "Biology of the Pancreas in Growing Animals" (S G Pierzynowski & R. Zabielski eds), Elsevier Science BV, Amsterdam, pp 381-393). A period of at least 4 weeks was allowed for recovery from surgery, before studies were commenced. Prior to study begin, the PEI status of each pig was confirmed via the stool chymotrypsin test (commercially available from Immundiagnostik AG, Wiesenstrasse 4, D-64625 Bensheim, Germany, with catalogue No. K6990).
Assay During the studies, the pigs were housed in modified metabolism cages on a 12:12 h light-dark cycle and allowed free access to water and fed two meals per day.
Test Meal The test meal contained 21.3% protein, 51.9% starch, 2.6% fat, and had the following composition (g/100 g dry matter):

Fish meal 3.5, poultry meat meal 10.2, wheat flour 29.5, shelled rice 14, potato starch 11, maize starch 14, casein 5.9, cellulose powder 4.3, vitamins, minerals and trace elements 7.6 (as per the nutritional requirement for pigs/piglets, see e.g. Table A of WO 01/58276).

Performance

To assess protease efficacy, the pigs were fed a single 250 g test meal mixed with 1 liter of water, 0.625 g $Cr_2O_3$ (chromic oxide marker) and into which differing amounts of reference protease of SEQ ID NO: 1 (0 mg, 20 mg, 50 mg and 120 mg enzyme protein, equivalent to 0, 500, 1250, and 3000 FIP U protease/meal) were mixed immediately before feeding.

For the trial itself, the protease variants of the invention were dosed according to mg enzyme protein (20 mg, 50 mg and 120 mg/meal), in order to compare the in vivo efficacy with that of the reference protease.

Ileal chyme was collected on ice for a total of 8 h after first appearance of the meal marker in the ileum (green chyme) and stored at −20° C. before analysis. At least one day washout was allowed between separate determinations.

Analysis

The frozen ileal chyme samples were freeze-dried, milled and analysed for dry matter (DM) and crude protein.

DM was estimated by weight after freeze-drying followed by 8 h incubation at 103° C.

Crude protein was calculated as nitrogen (N) multiplied by a factor 6.25, i.e. Crude protein (g/kg)=N (g/kg)×6.25 as stated in Animal Nutrition, 4th edition, Chapter 13 (Eds. P. McDonald, R. A. Edwards and J. F. D. Greenhalgh, Longman Scientific and Technical, 1988, ISBN 0-582-40903-9). The nitrogen content was determined with the Dumas combustion method (P G Wiles, I K Gray, R C Kissling, J AOAC Int. 1998 May-June; 81(3):620-32) using a "Vario MAX CNS" Elemental Analyzer (Elementar Analysensysteme GmbH).

$Cr_2O_3$ was oxidized to chromate and chromium content was calculated as described by Petry and Rapp in Zeitung für Tierphysiologie (1970), vol. 27, p. 181-189. (Petry & Rapp 1970; Z. Tierphysiol. 27; 181-189) via extinction at 365 nm (spectrophotometer).

Calculation of apparent pre-caecal protein digestibility was made by the marker method according to the formula:

$$\text{Ileal protein digestion (\%)} = 100 - \frac{[\% \ Cr_2O_3 \ \text{in feed}] \cdot [\% \ \text{protein in ileal chyme}]}{[\% \ Cr_2O_3 \ \text{in ileal chyme}] \cdot [\% \ \text{protein in feed}]} \cdot 100$$

in which $Cr_2O_3$ and protein were expressed as g/100 g dry matter.

Furthermore, the amount (mg) of protease required to achieve 50% and 60% protein digestibility (% CNA), respectively, were extrapolated from the individual regression curves (excel). In order to more efficiently compare with the 50% and 60% protein digestibility (% CNA) of the reference protease, a so-called Improvement Factor "IF" was calculated. An IF50 and IF60 value for each protease variant was determined by dividing the amount (mg) of reference protease required to achieve 50% and 60% protein digestibility (% CNA), by the amount (mg) of variant protease required to achieve 50% and 60% protein digestibility (% CNA), respectively.

Results and Conclusion

The Ileal protein digestion results are shown in the following Table 3. The protease dosage is indicated in milligram of enzyme protein per meal (mg/meal).

All the variants mentioned in Table 4 were also tested. They all had an IF of 0.8 or more.

TABLE 3

Influence of enzyme supplementation on apparent protein digestibility

| Variant | 0 | 20 mg enzyme protein/meal** | 50 mg enzyme protein/meal** | 120 mg enzyme protein/meal** | Calculated mg enzyme for 50% CNA | Calculated mg enzyme for 60% CNA | Improvement Factor in comparison to reference protease IF50 | Improvement Factor in comparison to reference protease IF60 |
|---|---|---|---|---|---|---|---|---|
| No protease | 12.82 | | | | | | | |
| Control animals (not PEI) | 76.3 | | | | | | | |
| Reference protease** | | 34.42 ± 6.46* | 47.14 ± 8.45* | 62.76 ± 2.65* | 55.57 | 104.29 | 1.00 | 1.00 |
| VAR294 | | 29.90 | 59.40 | 65.64 | 45.87 | 71.32 | 1.21 | 1.46 |
| VAR295 | | 36.96 | 59.19 | 65.53 | 39.49 | 69.90 | 1.41 | 1.49 |
| VAR375 | | 41.37 | 56.47 | 62.32 | 37.54 | 84.04 | 1.48 | 1.24 |
| VAR213 | | 33.92 | 53.29 | 61.89 | 50.24 | 92.67 | 1.11 | 1.13 |
| VAR307 | | 36.79 | 52.14 | 62.71 | 47.51 | 94.20 | 1.17 | 1.11 |
| N47H, G48D | | 33.78 | 51.52 | 64.90 | 49.14 | 87.11 | 1.13 | 1.20 |

*Standard Deviation calculated from 4 independent tests
**FIP U of reference protease: 500, 1250 and 3000 FIP Units Example 5

Pharmaceutical Protease Compositions

Pellets

A liquid concentrate of protease variant VAR295 (SEQ ID NO: 7) is prepared as described in Example 2. The liquid concentrate is germ-filtered and spray-dried, and the protease protein content of the dried powder is measured. The protease protein content is preferably above 50% (according to regulatory requirements). 500 g of dry protease powder is premixed together with 200 g microcrystalline cellulose and 300 g polyethylene glycol 4000 (Macrogol™ 4000) in a commercially available mixer. A sufficient amount of a commonly used wetting agent is added and the resulting wet mass is thoroughly mixed at room temperature. The homogenized mass is then extruded in a commercially available extruder, which is fitted with a piercing die having a certain hole diameter, e.g. of about 0.8 mm, to form cylindrical pellets. The extrudate produced is rounded to spherical pellets with a commercially available spheronizer by adding the necessary amount of a commonly used wetting agent. The pellets are dried at a product temperature of approximately 40° C. in a commercially available vacuum dryer. The dried pellets are then separated by using a mechanical sieving machine with appropriately sized screens, e.g. with 0.7 and 1.4 mm screens, to obtain the desired sieve fractions. The collected sieve fractions, e.g. of >0.7 mm and ≦1.4 mm, are collected and filled in portions comprising a desired standardized active substance content into capsules of appropriate size.

The resulting pellets are tested for proteolytic activity by applying the FIP method for proteases from pancreas powder with the modification that the activation step is omitted as described in Example 1.

The resulting pellets are then tested for disintegration according to Pharm. Eur. 2.9.1. (Section "Disintegration of tablets and capsules") (test solution: water—500 mL, 37° C.).

Example 6

In Vitro Toxicity

Cell assays with human colon adenocarcinoma cell lines were used for in vitro screening of the toxicity of proteases. The assays measure metabolic capacity of the cells and hence viability.

In vitro toxicity assay with HT-29 and Caco-2 cells

HT-29 cells (ACC 299 from German collection of microorganisms and Cell Cultures, DSMZ) were cultured in McCoy's 5A medium (Cambrex) supplemented with 10% FBS (Sigma, cat. no. F-6178). For the experiments cells were cultured at a density of $4·10^4$ cells/well/200 µl in 96 well culture plates. After 24 hours of adaptation of the cells to the wells, test components (proteases) were added in serum-free medium (DMEM:F12, Invitrogen) supplemented with 0.5 g/l probumin (Millipore), 1% Insulin/transferrin/selenium supplement (Invitrogen) and 1% penicillin and streptomycin (Invitrogen) in 2-fold dilutions in triplicates in nine different concentrations (weight/volume enzyme protein) and incubated another 24 hours. Viability was measured by metabolic capacity of the cells by using Alamar Blue (Invitrogen) measurements. Caco-2 cells were cultured in DMEM (Invitrogen 11960-044) supplemented with 10% fetal calf serum, 2 mM glutamine and 1% non-essential amino acids and grown in a humidified 5% $CO_2$ atmosphere. For the experiments cells were cultured at a density of $3·10^4$ cells/well/200 µl in 96 well plates. After 24 hours of adaptation to the wells, test components were added in serum-free medium to avoid binding of proteases by protease inhibitors present in serum and incubated another 24 hours, where after viability were measured. Cell viability was measured by measuring the ability of Alamar Blue to be metabolized by cells. All experiments with testing of protease variants were done under serum-free conditions.

Maximum metabolic activity is observed in wells without any protease added (and is set to 100%). The concentration at which 50% of the maximum metabolic activity is obtained for the tested protease is divided by the concentration at which 50% of the maximum metabolic activity is obtained for the reference protease and the resulting "toxicity ratio" is apparent from Table 4 below. The higher the concentration, the less toxic; and the higher the ratio to the reference protease, the more is the toxicity reduced. Accordingly, the toxicity of protease VAR203 is reduced as compared to the reference protease. Variants have been tested on both Caco-2 and HT-29 cells.

TABLE 4

| Variant | Toxicity | |
|---|---|---|
| | HT-29 | Caco-2 |
| Reference protease (wild type) | 1 | 1 |
| S69T + E125D (VAR203) | 1.7 | Not tested |
| T41A, T68R, V88A | 1.4 | >2 |
| G12D | 2.1 | 1.4 |
| N47H, G48D | 2.3 | 2.3 |
| G12N, T22A, N23D, N47T, R165H | 2.7 | 2.8 |
| R14I, R38T, T151I | 1.6 | 2.3 |
| G34A, T68A, R165T | 1.2 | 1.4 |
| A1T, N47S, Q54L, T68S, R165G, T166A | 1.1 | 1.0 |
| R38T, E53K, L73P | 1.1 | 1.4 |

Example 7

In vitro digestion performance

The performance of protease VAR203 (SEQ ID NO: 11) and the other variants mentioned in Table 4 were determined in an in vitro digestion model comprising a 1 h pH 3 (stomach) step as well as a 2 h pH 6 (intestinal) step and compared to the performance of the reference protease (SEQ ID NO: 1). The proteases were purified as described in Example 2, and the content of enzyme protein in mg/ml was determined by $A_{280}$.

The diet, which is identical to the test meal of Example 4, was dissolved in 0.1 M HCl giving a working slurry of 0.2 g diet/ml. pH was adjusted to pH 2.5 with HCl. 100 µl diet slurry was added to each well in MTP (Micro Titer Plates) and mixed with 20 µl pepsin (Merck VL 317492437, catalogue no. 1.0792.0001, 700 mg/l, final concentration of 93 µg/ml) and 30 µl diluted enzyme (diluted to 10 µM (0.2 mg/ml)). Final pH in all wells was 2.8 to 3.0. A duplicate of 4 concentrations (0.2, 0.1, 0.05 and 0.025 mg/ml) were made for each enzyme (diluted in 20 mM Acetate, 0.01% Triton X-100, pH5). This incubated at 37° C. for 1 h, 750 rpm (Eppendorf Thermomixer) and is defined as the gastric step of in vitro digestion model.

To start the intestinal step, pH was raised to 6.0 to 6.05 by adding 25 µl buffer (0.8M MES, 0.8M imidazole, 0.8M Acetate, mixed 40%/60% pH 5/9) to each well. In addition, 25 µl bile salts (80 mM Bile salts, bile salt mixture from Solvay Pharmaceuticals, batch 176.01-PA-7374, dissolved in deionized water, Millipore milliQ) were added to a final concentration of 10 mM, following incubation at 37° C., 750 rpm, for 2 h. The intestinal step was terminated by separating the proteases from diet slurry by centrifugation at 2700 rpm, 4° C. for 10 min.

Protease activity was determined by quantification of free amino groups in supernatants using the OPA method (O-phthaldialdehyde). The number of free amino acids in wells with enzyme substratced from 'pepsin only' wells reflects protease performance. Supernatants were diluted 10× in enzyme dilution buffer (20 mM Acetate pH5, 0.01% Triton X-100), and 20 µl diluted supernatants were mixed with 200 µl OPA reagent (3.81 g di-sodium tetraborate decahydrate, 1 mL 10% SDS, 88 mg DTT was mixed, and 80 mg OPA dissolved in 2 mL 96% ethanol was added before addition of deionized water to a total volume of 100 ml). Serine dilution row (0.5 mg/ml stock is diluted 2-fold) was included as standard for quantification of free amino groups. Absorbance at 340 nm was measured.

The calculation of an apparent improvement factor (IF) of the tested variant relative to the reference protease is carried out by fitting the absolute data of hydrolysed amino groups (obtained by the OPA determination) corrected for no enzyme to a three-parameter logistic equation:

$$NH_2 = \frac{NH_2(\max)}{(1 + (I(50)/Conc)^\wedge \text{Slope})}$$

where $NH_2$ is the amount of free amino groups (mM), $NH_2$(max) is the maximal amount of free amino groups that the protease can liberate from the diet, conc is the protease concentration (mg enzyme per meal (250 g)), slope is the slope of the parallel curves (see below) and I(50) is the variable from which the IF is calculated. The inverted V means exp. $NH_2$(max) was determined experimentally to 20 mM using very high dosages of the reference protease.

In order to fit the obtained data to this equation, two assumptions are made. First, it is assumed that all obtained curves of hydrolysed amino groups versus mg enzyme dosed are parallel (slope constant). Second, substrate availability is the limiting factor of activity and a plateau of the amount of hydrolysed amino groups ($NH_2$(max)) will therefore be obtained at significantly high enzyme concentrations. The improvement factor (IF) is defined as:

IF=$I$(50)(reference)/$I$(50)(variant)

where I(50)(reference) is the concentration of reference enzyme needed to obtain half $NH_2$(max) and I(50)(variant) is the variant concentration needed to obtain half $NH_2$(max).

The protease variant VAR203 has an improvement factor of 2.6, the reference protease has, by definition, an improvement factor of 1.0. This means that a 2.6 times lower amount of the VAR203 protease is required in order to obtain a similar effect as the reference protease. All variants listed in Table 4 had an IF of 0.7 or more.

Example 8

Toxicological Evaluation Using the Stomach-Catheterised Rat Model

Test System

Experience has shown increased risk of regurgitation of test article with subsequent risk of unintended exposure to the lungs following oral administration by gavage of proteases to rats. Therefore a specialized experimental methodology was used to distinguish the in vivo toxicity of the protease variants from the wild type (SEQ ID No: 1) on the gastro-intestinal tract. Stomach-catheterised rats supplied by Charles River Laboratories Germany GmbH were used in these experiments. The test articles were administered daily for 14 days via a stomach-catheter directly into the stomach eliminating the risk of mis-dosing into the trachea and decreasing the risk of regurgitation of test article from the stomach. The application volume was 10 mL/kg for all proteases and food was withdrawn approximately 4 hours before administration and offered again 4 hours after dosing. The animals were housed singly and to prevent blockage of the catheter; it was rinsed with tap water after each administration and once weekly in the afternoon.

Measurements

The rats were observed individually before and after dosing for any signs of behavioural changes, reaction to treatment or illness. The body temperature of all animals was measured with an anal probe three times during the study at pre-dose and 1 hour after dosing. The body weight and food consumption were measured at weekly intervals and the water consumption by daily visual inspection of the water bottles.

At termination all animals were subjected to a detailed autopsy and histopathology was performed on potential target organs including the stomach, trachea and lungs.

Results

The mortality observed in the present studies is predominantly related to regurgitation of the test articles into the respiration tract and also to technical issues including leakage of test article from the applications site (stomach). The mortality is most predominant in the wild type protease treated group at a dose level of 700 mg/kg.

In the histopathological examination, fore-stomach inflammation associated with squamous cell hyperplasia of the epithelium is considered the target toxicity. Based on these test article induced local effects on the stomach mucosa, the wild type protease is more toxic compared with the variants as a group.

In conclusion, the mortality and histopathology data in combination show that the wild type is more toxic than the variants.

TABLE 5

Mortality rate of wild type and variants in 14 days toxicity studies

| Protease | Dose (mg/kg/day) | Rats died/treated | % mortality |
|---|---|---|---|
| Control (negative) | | 0/11 | 0 |
| Wild type | 700 | 4/6 | 67 |
| G12D | 810 | 1/8 | 13 |
| G12N, T22A, N23D, N47T, R165H | 1000 | 0/6 | 0 |
| R14I, R38T, T151I | 1000 | 0/6 | 0 |
| N47H, G48D | 1000 | 0/6 | 0 |

TABLE 6

Histopathological irritation findings (given as number of affected animals) in gastric-catheterised male rats

| | Control (negative) | Wild type | G12D | G12N, T22A, N23D, N47T, R165H | R14I, R38T, T151I | N47H, G48D |
|---|---|---|---|---|---|---|
| Dose (mg/kg/day) | | 500 | 500/810 | 1000 | 1000 | 1000 |
| Number | 11 | 17 | 8/8 | 6 | 6 | 6 |

TABLE 6-continued

Histopathological irritation findings (given as number of affected animals) in gastric-catheterised male rats

|  | Control (negative) | Wild type | G12D | G12N, T22A, N23D, N47T, R165H | R14I, R38T, T151I | N47H, G48D |
|---|---|---|---|---|---|---|
| Squamous cell hyperplasia | 0 | 11 | 0/0 | 3 | 6 | 5 |
| Mononuclear cell infiltration | 2 | 3 | 0/0 | 1 | 1 | 0 |
| Forestomach inflammation | 0 | 8 | 0/0 | 1 | 1 | 2 |

---

The invention claimed is:

1. A non-naturally-occurring protease having at least 90% sequence identity to the sequence of amino acids 1-188 of SEQ ID NO:1, and which, as compared to amino acids 1-188 of SEQ ID NO:1, comprises at least one substitution selected from the group consisting of A1T; I3V; T41A; E53K; Q54L; Q54D; S99P; P124L; M131V; and T151I.

2. The protease of claim 1, which comprises A1T.

3. The protease of claim 1, which comprises I3V.

4. The protease of claim 1, which comprises T41A.

5. The protease of claim 1, which comprises E53K.

6. The protease of claim 1, which comprises Q54L or Q54D.

7. The protease of claim 1, which comprises S99P.

8. The protease of claim 1, which comprises P124L.

9. The protease of claim 1, which comprises M131V.

10. The protease of claim 1, which comprises T151I.

11. The protease of claim 1, which has at least 95% identity to amino acids 1-188 of SEQ ID NO:1.

12. A pharmaceutical composition comprising a protease of claim 1 and at least one pharmaceutically acceptable auxiliary material.

13. The composition of claim 12, further comprising a lipase or an amylase.

14. The composition of claim 13, wherein
   (a) the lipase has at least 70% identity to a lipase having amino acids 1-269 of SEQ ID NO:2; and/or
   (b) the amylase has at least 70% identity to an amylase selected from the group consisting of
      (i) an amylase having amino acids 1-481 of SEQ ID NO:3,
      (ii) an amylase having amino acids 1-483 of SEQ ID NO:4, and
      (iii) an amylase having amino acids 1-513 of SEQ ID NO:5.

15. A feed composition comprising the protease of claim 1.

16. A method for the treatment of digestive disorders, pancreatic exocrine insufficiency, pancreatitis, cystic fibrosis, diabetes type I, and/or diabetes type II, comprising administering a therapeutically effective amount of a protease of claim 1.

17. The method of claim 16, further comprising administering a therapeutically effective amount of a lipase or an amylase.

* * * * *